(12) United States Patent
Blank et al.

(10) Patent No.: US 7,606,608 B2
(45) Date of Patent: Oct. 20, 2009

(54) OPTICAL SAMPLING INTERFACE SYSTEM FOR IN-VIVO MEASUREMENT OF TISSUE

(75) Inventors: Thomas B. Blank, Chandler, AZ (US);
George Acosta, Phoenix, AZ (US);
Mutua Mattu, Gilbert, AZ (US); Marcy Makarewicz, Chandler, AZ (US);
Stephen L. Monfre, Gilbert, AZ (US);
Alexander D. Lorenz, Phoenix, AZ (US); Timothy L. Ruchti, Gilbert, AZ (US); Kevin H. Hazen, Phoenix, AZ (US); Donovan D. Berry, Tempe, AZ (US); Roxanne E. Abul-Haj, Mesa, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 660 days.

(21) Appl. No.: 11/008,001

(22) Filed: Dec. 8, 2004

(65) Prior Publication Data

US 2005/0203359 A1    Sep. 15, 2005

(51) Int. Cl.
*A61B 5/1455* (2006.01)
(52) U.S. Cl. .................................... 600/344
(58) Field of Classification Search ........... 600/310, 600/322, 316, 340, 344
See application file for complete search history.

(56) References Cited

U.S. PATENT DOCUMENTS

| 4,033,054 | A | 7/1977 | Fukuoka |
| 4,213,462 | A | 7/1980 | Sato |
| 4,272,040 | A | 6/1981 | Bastian et al. |
| 4,321,930 | A | 3/1982 | Jobsis et al. |
| 4,548,505 | A | 10/1985 | Ono |
| 4,674,338 | A | 6/1987 | Carpenter |
| 4,798,955 | A | 1/1989 | Rosenthal |
| 4,830,014 | A | 5/1989 | Goodman et al. |
| 4,866,644 | A | 9/1989 | Shenk |
| 4,882,492 | A | 11/1989 | Schlager |
| 5,007,423 | A | 4/1991 | Branstetter |
| 5,068,536 | A | 11/1991 | Rosenthal |
| 5,070,874 | A | 12/1991 | Barnes et al. |
| 5,131,391 | A | 7/1992 | Sakai |

(Continued)

FOREIGN PATENT DOCUMENTS

CN    1214768    4/1999

(Continued)

OTHER PUBLICATIONS

Barnes, R.J. et al. "Standard Normal Variate Transformation and De-trending of Near-Infrared Diffuse Reflectance Spectra," *Applied Spectroscopy*, 43, pp. 772-777, 1989.

(Continued)

*Primary Examiner*—Eric F Winakur
(74) *Attorney, Agent, or Firm*—Michael A. Glenn; Glenn Patent Group

(57) ABSTRACT

An optical sampling interface system is disclosed that minimizes and compensates for errors that result from sampling variations and measurement site state fluctuations. Embodiments of the invention use a guide that does at least one of, induce the formation of a tissue meniscus, minimize interference due to surface irregularities, control variation in the volume of tissue sampled, use a two-part guide system, use a guide that controls rotation of a sample probe and allows z-axis movement of the probe, use a separate base module and sample module in conjunction with a guide, and use a guide that controls rotation. Optional components include an occlusive element and a coupling fluid.

7 Claims, 8 Drawing Sheets

U.S. PATENT DOCUMENTS

| | | | |
|---|---|---|---|
| 5,170,786 A | 12/1992 | Thomas et al. |
| 5,285,783 A | 2/1994 | Secker |
| 5,299,570 A | 4/1994 | Hatschek |
| 5,348,003 A | 9/1994 | Caro |
| 5,361,758 A | 11/1994 | Hall |
| 5,398,681 A | 3/1995 | Kupershmidt |
| 5,448,662 A | 9/1995 | Kittel et al. |
| 5,492,118 A | 2/1996 | Gratton |
| 5,506,482 A | 4/1996 | Teramatsu et al. |
| 5,507,288 A | 4/1996 | Bocker et al. |
| 5,517,301 A | 5/1996 | Dave |
| 5,548,674 A | 8/1996 | Rondeau |
| 5,574,855 A | 11/1996 | Rosich et al. |
| 5,596,987 A | 1/1997 | Chance |
| 5,619,195 A | 4/1997 | Allen et al. |
| 5,632,273 A | 5/1997 | Suzuki |
| 5,636,634 A | 6/1997 | Kordis et al. |
| 5,655,530 A | 8/1997 | Messerschmidt |
| 5,661,843 A | 8/1997 | Rickemback et al. |
| 5,671,317 A | 9/1997 | Weishaupt |
| 5,687,717 A | 11/1997 | Halpern |
| 5,725,480 A | 3/1998 | Ooste |
| 5,730,140 A | 3/1998 | Fitch |
| 5,747,806 A | 5/1998 | Khalil |
| 5,750,994 A | 5/1998 | Schlager |
| 5,769,076 A | 6/1998 | Maekawa et al. |
| 5,770,454 A | 6/1998 | Essenpreis |
| 5,823,951 A | 10/1998 | Messerschmidt |
| 5,825,488 A | 10/1998 | Kohl |
| 5,825,951 A | 10/1998 | Kitamura |
| 5,830,132 A | 11/1998 | Robinson |
| 5,869,075 A | 2/1999 | Krzysik |
| 5,877,664 A | 3/1999 | Jackson |
| 5,879,373 A | 3/1999 | Roper |
| 5,891,021 A | 4/1999 | Dillon et al. |
| 5,912,656 A | 6/1999 | Tham et al. |
| 5,935,062 A | 8/1999 | Messerschmidt |
| 5,945,676 A | 8/1999 | Khalil |
| 5,956,150 A | 9/1999 | Kanne |
| 5,978,691 A | 11/1999 | Mills |
| 6,014,756 A | 1/2000 | Dottling |
| 6,040,578 A | 3/2000 | Malin |
| 6,045,511 A | 4/2000 | Ott |
| 6,067,463 A | 5/2000 | Jeng |
| 6,088,605 A | 7/2000 | Griffith |
| 6,093,156 A | 7/2000 | Cunningham |
| 6,095,974 A | 8/2000 | Shemwell |
| 6,115,673 A | 9/2000 | Malin |
| 6,144,868 A | 11/2000 | Parker |
| 6,152,876 A | 11/2000 | Robinson |
| 6,157,041 A | 12/2000 | Thomas |
| 6,180,416 B1 | 1/2001 | Kuenik |
| 6,230,034 B1 | 5/2001 | Messerschmidt |
| 6,233,471 B1 | 5/2001 | Berner |
| 6,236,047 B1 | 5/2001 | Malin |
| 6,240,306 B1 | 5/2001 | Rohrscheib et al. |
| 6,253,097 B1 | 6/2001 | Aronow et al. |
| 6,272,364 B1 | 8/2001 | Kurnik |
| 6,280,381 B1 | 8/2001 | Malin |
| 6,289,230 B1 | 9/2001 | Chaiken |
| 6,304,766 B1 | 10/2001 | Colvin, Jr. |
| 6,326,160 B1 | 12/2001 | Dunn |
| 6,330,464 B1 | 12/2001 | Colvin, Jr. |
| 6,334,360 B1 | 1/2002 | Chen |
| 6,381,489 B1 | 4/2002 | Ashibe |
| 6,400,974 B1 | 6/2002 | Lesho |
| 6,405,065 B1 | 6/2002 | Malin |
| 6,411,373 B1 | 6/2002 | Garside |
| 6,411,838 B1 | 6/2002 | Nordstrom et al. |
| 6,415,167 B1 | 7/2002 | Blank |
| 6,421,549 B1 | 7/2002 | Jacques |
| 6,441,388 B1 | 8/2002 | Thomas |
| 6,442,408 B1 | 8/2002 | Wenzel |
| 6,449,500 B1 | 9/2002 | Asai |
| 6,456,870 B1 | 9/2002 | Rennert |
| 6,475,800 B1 | 11/2002 | Hazen |
| 6,487,429 B2 | 11/2002 | Hockersmith |
| 6,493,566 B1 | 12/2002 | Ruchti |
| 6,501,982 B1 | 12/2002 | Ruchti |
| 6,507,687 B1 | 1/2003 | Juskaitis et al. |
| 6,512,937 B2 | 1/2003 | Blank |
| 6,512,982 B2 | 1/2003 | Yang |
| 6,528,809 B1 | 3/2003 | Thomas |
| 6,546,269 B1 | 4/2003 | Kurnik |
| 6,585,370 B2 | 7/2003 | Zelman |
| 6,631,282 B2 | 10/2003 | Rule et al. |
| 6,641,533 B2 | 11/2003 | Causey, III et al. |
| 6,690,958 B1 | 2/2004 | Walker et al. |
| 6,788,965 B2 | 9/2004 | Ruchti |
| 6,839,583 B1 | 1/2005 | Lewandowski et al. |
| 6,927,843 B2 | 8/2005 | Dick |
| 7,133,710 B2 | 11/2006 | Acosta et al. |
| 7,178,063 B1 | 2/2007 | Smith |
| 7,409,330 B2 | 8/2008 | Kumamoto |
| 2002/0026106 A1 | 2/2002 | Khalil et al. |
| 2002/0058864 A1 | 5/2002 | Mansfield |
| 2002/0087949 A1 | 7/2002 | Golender et al. |
| 2003/0040663 A1 | 2/2003 | Rule et al. |
| 2003/0156270 A1 | 8/2003 | Hunter |
| 2003/0216627 A1 | 11/2003 | Lorenz |
| 2003/0216630 A1 | 11/2003 | Jersey-Willuhn et al. |
| 2004/0068163 A1 | 4/2004 | Ruchti |
| 2004/0077937 A1 | 4/2004 | Yarden |
| 2004/0127777 A1 | 7/2004 | Ruchti |
| 2004/0163032 A1 | 8/2004 | Guo |
| 2004/0167473 A1 | 8/2004 | Moenning |
| 2005/0007125 A1 | 1/2005 | Heger |
| 2005/0034102 A1 | 2/2005 | Peck |
| 2005/0187439 A1 | 8/2005 | Blank et al. |
| 2005/0267342 A1 | 12/2005 | Blank et al. |
| 2006/0200017 A1 | 9/2006 | Monfre et al. |
| 2006/0211931 A1 | 9/2006 | Blank et al. |
| 2006/0217602 A1 | 9/2006 | Abul-Haj et al. |
| 2008/0009835 A1 | 1/2008 | Kriesel et al. |
| 2008/0033275 A1 | 2/2008 | Blank et al. |

FOREIGN PATENT DOCUMENTS

| | | |
|---|---|---|
| DE | 26 40 987 | 3/1978 |
| EP | 1254631 | 11/2002 |
| JP | 05-317295 | 12/1993 |
| JP | 08-215180 | 8/1996 |
| JP | 2001-037741 | 2/2001 |
| JP | 2001-299727 | 10/2001 |
| JP | 1992-215742 | 10/2002 |
| JP | 2002535023 | 10/2002 |
| WO | WO96/28084 | 9/1996 |
| WO | WO97/05819 | 2/1997 |
| WO | WO 97/28437 | 8/1997 |
| WO | WO00/22982 | 4/2000 |
| WO | WO00/42907 | 7/2000 |
| WO | WO 00/74562 | 12/2000 |
| WO | WO00/76575 | 12/2000 |
| WO | WO 01/31304 | 5/2001 |
| WO | WO 01/58355 | 8/2001 |
| WO | WO 01/72222 | 10/2001 |

OTHER PUBLICATIONS

Beebe, K.R. et al., "Chemometrics A Practical Guide," New York: John Wiley & Sons, Inc., 1998.

Blank, T. B. et al. "Transfer of near-infrared multivariate calibrations without standards," *Analytical Chemistry*, 68, pp. 2987-2995, 1996.

Diabetes Statistics. Bethesda, MD: National Institute of Health, Publication No. 98-3926, Nov. 1997.

Geladi, P. et al. "Linearization and Scatter-Correction for Near-Infrared Reflectance Spectra of Meat," *Applied Spectroscopy*, vol. 39, pp. 491-500, 1985.

Gross, T.M. et al. "Performance Evaluation of the MiniMed Continuous Glucose Monitoring System During Patient Home Use", *Diabetes Technology & Therapeutics*, 2, 2000, 49-56.

"GlucoWatch Automatic Glucose Biographer and AutoSensors", Cygnus Inc., Document #1992-00, Rev. Mar. 2001.

Hazen, Kevin H. "Glucose Determination in Biological Matrices Using Near-Infrared Spectr Sage, Burton H. "FDA Panel Approves Cygnus's Noninvasive GlucoWatch™", *Diabetes Technology & Therapeutics*, 2, 2000, 115-116.oscopy", doctoral dissertation, University of Iowa, 1995.

Isaksson, T. et al. "Optimised scaling (OS-2) regression applied to near infrared . . . food products," *J. Near Infrared Spectroscopy*, 1, pp. 85-97, 1993.

Isaksson, T. et al. "Piece-Wise Multiplicative Scatter Correction Applied to Near-Infrared Diffuse Transmittance Data From Meat Products", *Applied Spectroscopy*, 47, pp. 702-709, 1993.

Martens, H. et al. "Extended multiplicative signal correction and spectral interference subtraction: new preprocessing methods for near infrared spectroscopy", J. Pharm Biomed Anal, 9, pp. 625-635, 1991.

Massart, D.L. et al. "Chemometrics: a textbook," New York: Elsevier Science Publishing Company, Inc., 1990.

Ohkubo, Y. et al. "Intensive insulin therapy prevents the progression of diabetic microvascular complications in Japanese patients with non-insulin-dependent diabetes mellitus: a randomized prospective 6-year study," *Diabetes Res Clin Pract*, vol. 28, pp. 103-117, 1995.

Oppenheim, A.V. et al. "Digital Signal Processing," Englewood Cliffs, NJ: Prentice Hall, 1975, pp. 195-271.

Otto, M., "Statistics and Computer Application in Analytical Chemistry," Chemometrics, Weinheim: Wiley-VCH, 1999.

Rebrin et al. "Subcutaneous Glucose Predicts Plasma Glucose Independent of Insulin: Implications for Continuous Monitoring", *Am., J. Physiol.*, 277, 1999, E561-E571, 0193-1849/99, The American Physiological Society, 1999.

Savitzky, A. et al. "Smoothing and Differentiation of Data by Simplified Least Squares Procedures," Anal. Chem., vol. 36, No. 8, pp. 1627-1639, 1964.

Sharaf, M.A. et al., Chemometrics, New York: John Wiley & Sons, Inc., 1996.

Sum, S.T. et al. "Standardization of Fiber-Optic Probes for Near-Infrared Multivariate Calibrations," Applied Spectroscopy, vol. 52, No. 6, pp. 869-877, 1998.

Sum, S.T., "Spectral Signal Correction for Multivariate Calibration," Doctoral Disseration, University of Delaware, Summer 1998.

Tamada, J.A. et al. "Noninvasive Glucose Monitoring Comprehensive Clinical Results," *JAMA*, vol. 282, No. 19, pp. 1839-1844, Nov. 17, 1999.

The Diabetes Control and Complications Trial Research Group. "The effect of intensive treatment of diabetes on the development and progression of long-term complications in insulin-dependent diabetes mellitus." N Eng J of Med 1993;329:977-86.

Trajanowski, Z. et al. "Open-Flow Microperfusion of Subcutaneous Adipose Tissue for On-Line Continuous Ex Vivo Measurement of Glucose Concentration", *Diabetes Care*, 20, 1997, 1114-1120.

Trajanowski, Z. et al. "Portable Device for Continuous Fractionated Blood Sampling and Continuous ex vivo Blood Glucose Monitoring", *Biosensors and Bioelectronics*, 11, 1996, 479-487.

U.K. Prospective Diabetes Study (UKPDS) Group, "Intensive blood-glucose control with sulphonylureas or insulin compared with conventional treatment and risk of complications in patients with type 2 diabetes," *Lancet*, vol. 352, pp. 837-853, 1998.

Webster's II New Riverside University Dictionary; The Riverside Publishing Company; 1994; p. 1000.

OPTICAL SAMPLING INTERFACE SYSTEM FOR IN-VIVO MEASUREMENT OF TISSUE

BACKGROUND OF THE INVENTION

1. Technical Field

The invention relates to optical sampling of tissue in-vivo. More particularly, the invention relates to an optical sampling interface system that includes an optical probe placement guide, a means for stabilizing the sampled tissue, an optical coupler for repeatably sampling a tissue measurement site in-vivo, and/or a means for compensating for measurement bias.

2. Description of the Prior Art

In-vivo measurement of tissue properties and analytes using optical based analyzers requires that a tissue measurement region be positioned and coupled with respect to an optical interface or probe. The requirements of an optical sampling interface system for such placement and coupling depends upon the nature of the tissue properties and analytes under consideration, the optical technology being applied, and the variability of the tissue with respect to the target analyte. Often, when sampling reproducibility is vital, the optical measurement is performed in a laboratory where the majority of the factors pertaining to the measurement are controlled or constrained. However, there are many demanding in-vivo applications that cannot be performed in a laboratory setting, but yet require a high degree of optical sampling reproducibility. In one example, a relatively unskilled operator or user must perform the optical measurement. One such application is the noninvasive estimation of glucose concentration through near-infrared spectroscopy. With the desired end result being an optical measurement system that is used by the consumer in a variety of environments, the optical sampling requirements are stringent. This problem is further considered through a discussion of the target application, the structure of live skin, and the dynamic properties of live tissue.

Diabetes

Diabetes is a chronic disease that results in abnormal production and use of insulin, a hormone that facilitates glucose uptake into cells. While a precise cause of diabetes is unknown, genetic factors, environmental factors, and obesity play roles. Diabetics have increased risk in three broad categories: cardiovascular heart disease, retinopathy, and neuropathy. Diabetics often have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance and hyperinsulinemia, which is also known as hypoglycemia.

Diabetes Prevalence and Trends

The prevalence of individuals with diabetes is increasing with time. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by 6% in 1999 and rose by 33% between 1990 and 1998. This corresponds to approximately eight hundred thousand new cases every year in America. The estimated total cost to the United States economy alone exceeds $90 billion per year. *Diabetes Statistics*, National Institutes of Health, Publication No. 98-3926, Bethesda, Md. (November 1997).

Noninvasive Estimation of Glucose Concentration

Numerous approaches have been explored for estimating blood glucose concentrations, ranging from invasive methods such as microdialysis to noninvasive technologies that rely on spectroscopy. Each method has associated advantages and disadvantages, but only a few have received approval from certifying agencies. To date, no noninvasive techniques for the self-monitoring of blood glucose concentration have been certified by the U.S. Food and Drug Administration.

One method, near-infrared spectroscopy, involves the illumination of a region of the body with near-infrared electromagnetic radiation, i.e. light in the wavelength range 700 to 2500 nm. The light is partially absorbed and scattered, according to its interaction with the tissue constituents prior to being reflected back to a detector. The detected light contains quantitative information that is based on the known interaction of the incident light with components of the body tissue including water, fat, protein, and glucose.

Previously reported methods for the noninvasive estimation of glucose concentration through near-infrared spectroscopy rely on the detection of the magnitude of light attenuation caused by the absorption signature of blood glucose as represented in the targeted tissue volume. The targeted tissue volume is that portion of irradiated tissue from which light is reflected or transmitted to the spectrometer detection system. The signal due to the absorption of glucose is extracted from the spectral measurement through various methods of signal processing and one or more mathematical models. The models are developed through the process of calibration on the basis of an exemplary set of spectral measurements and associated reference blood glucose concentrations (the calibration set) based on an analysis of capillary (fingertip) blood, venous blood, and/or alternative site fluids.

Near-infrared spectroscopy has been demonstrated in specific studies to represent a possible approach for the noninvasive measurement of blood glucose levels. M. Robinson, R. Eaton, D. Haaland, G. Keep, E. Thomas, B. Stalled, P. Robinson, *Noninvasive glucose monitoring in diabetic patients: A preliminary evaluation*, Clin Chem, 38: 1618-22 (1992) reports three different instrument configurations for measuring diffuse transmittance through the finger in the 600-1300 nm range. Meal tolerance tests were used to perturb the glucose concentrations of three subjects and calibration models were constructed specific to each subject on single days and tested through cross-validation. Absolute average prediction errors ranged from 19.8 to 37.8 mg/dL. H. Heise, R. Marbach, T. Koschinsky, F. Gries, *Noninvasive blood glucose sensors based on near-infrared spectroscopy*, Artif Org, 18: 439-47 (1994); H. Heise, R. Marbach, *Effect of data pretreatment on the noninvasive blood glucose measurement by diffuse reflectance near-IR spectroscopy*, SPIE Proc, 2089: 114-5 (1994); R. Marbach, T. Koschinsky, F. Gries, H. Heise, *Noninvasive glucose assay by near-infrared diffuse reflectance spectroscopy of the human inner lip*, Appl Spectrosc, 47: 875-81 (1993); and R. Marbach, H. Heise, *Optical diffuse reflectance accessory for measurements of skin tissue by near-infrared spectroscopy*, Applied Optics 34(4): 610-21 (1995) present results through a diffuse reflectance measurement of the oral mucosa in the 1111 to 1835 nm range with an optimized diffuse reflectance accessory. In-vivo experiments were conducted on single diabetics using glucose tolerance tests and on a population of 133 different subjects. The best standard error of estimation reported was 43 mg/dL and was obtained from a two-day single person oral glucose tolerance test that was evaluated through cross-validation.

K. Jagemann, C. Fischbacker, K. Danzer, U. Muller, B. Mertes, *Application of near-infrared spectroscopy for noninvasive determination of blood/tissue glucose using neural network*, Z Phys Chem, 191S: 179-190 (1995); C. Fischbacker, K. Jagemann, K. Danzer, U. Muller, L. Papenkrodt, J. Schuler, *Enhancing calibration models for noninvasive near-infrared spectroscopic blood glucose determinations*, Fresenius J Anal Chem 359: 78-82 (1997); K. Danzer, C. Fischbacker, K. Jagemann, K. Reichelt, *Near-infrared diffuse reflection spectroscopy for noninvasive blood-glucose monitoring*, LEOS Newsletter 12(2): 9-11 (1998); and U. Muller, B. Mertes, C. Fischbacker, K. Jagemann, K. Danzer, *Noninvasive blood glucose monitoring by means of new infrared spectroscopic methods for improving the reliability of the calibration models*, Int J Artif Organs, 20: 285-290 (1997) recorded spectra in diffuse reflectance over the 800 to 1350 nm range on the middle finger of the right hand with a fiber-optic probe. Each experiment involved a diabetic subject and was conducted over a single day with perturbation of blood glucose concentrations through carbohydrate loading. Results, using both partial least squares regression and radial basis function neural networks, were evaluated on single subjects over single days through cross-validation. Danzer, et al., supra, report an average root mean square measurement error of 36 mg/dL through cross-validation over 31 glucose concentration profiles.

J. Burmeister, M. Arnold, G. Small, *Human noninvasive measurement of glucose using near infrared spectroscopy* [abstract], Pittcon, New Orleans La. (1998) collected absorbance spectra through a transmission measurement of the tongue in the 1429 to 2000 nm range. A study of five diabetic subjects was conducted over a 39-day period with five samples taken per day. Every fifth sample was used for an independent test set and the standard error of estimation for all subjects was greater than 54 mg/dL.

T. Blank, T. Ruchti, S. Malin, S. Monfre, *The use of near-infrared diffuse reflectance for the noninvasive prediction of blood glucose*, IEEE Lasers and Electro-Optics Society Newsletter, 13: 5 (October 1999), report studies that demonstrate noninvasive estimation of blood glucose concentration during modified oral glucose tolerance tests over a short time period. The calibration was customized for the individual and tested over a relatively short time period.

In all of these studies, diverse limitations were cited that affect the acceptance of such a method as a commercial product. Fundamental to all the studies is the problem of the small signal attributable to glucose, particularly in view of the difficulty in obtaining a reproducible sample of a given tissue volume, as a result of the complex and dynamic nature of the tissue. For example, see O. Khalil, *Spectroscopic and clinical aspects of noninvasive glucose measurements*, Clin Chem, v. 45, pp. 165-77 (1999). The sampling problem is further accentuated by noting that the reported studies were performed under highly controlled conditions using skilled professionals rather than in a home environment by the consumer. As reported by S. Malin, T. Ruchti, *An Intelligent System for Noninvasive Blood Analyte Prediction*, U.S. Pat. No. 6,280,381 (Aug. 28, 2001), the entirety of which is hereby incorporated by reference, chemical, structural and physiological variations occur that produce dramatic and nonlinear changes in the optical properties of the tissue sample. See R. Anderson, J. Parrish, *The optics of human skin*, Journal of Investigative Dermatology, 7:1, pp. 13-19 (1981); W. Cheong, S. Prahl, A Welch, *A review of the optical properties of biological tissues*, IEEE Journal of Quantum Electronics, 26:12, pp. 2166-2185, (December 1990); D. Benaron, D. Ho, *Imaging (NIRI) and quantitation (NIRS) in tissue using time-resolved spectrophotometry: the impact of statically and dynamically variable optical path lengths*, SPIE, 1888, pp. 10-21 (1993); J. Conway, K. Norris, C. Bodwell, *A new approach for the estimation of body composition: infrared interactance*, The American Journal of Clinical Nutrition, 40, pp. 1123-1140 (December 1984); S. Homma, T. Fukunaga, A. Kagaya, *Influence of adipose tissue thickness in near infrared spectroscopic signals in the measurement of human muscle*, Journal of Biomedical Optics, 1:4, pp. 418-424 (October 1996); A Profio, *Light transport in tissue*, Applied Optics, 28:12), pp. 2216-2222, (June 1989), M. Van Gemert, S. Jacques, H. Sterenborg, W. Star, *Skin optics*, IEEE Transactions on Biomedical Engineering, 36:12, pp. 1146-1154 (December 1989); and B. Wilson, S. Jacques, *Optical reflectance and transmittance of tissues: principles and applications*, IEEE Journal of Quantum Electronics, 26:12, pp. 2186-2199.

The measurement is further complicated by the heterogeneity of the sample, the multi-layered structure of the skin, the rapid variation related to hydration levels, changes in the volume fraction of blood in the tissue, hormonal stimulation, temperature fluctuations, and changes in blood constituent concentrations. This is further considered through a discussion of the scattering properties of skin and the dynamic nature of the tissue.

Structure of Human Skin

The structure and pigmentation of human skin varies widely among individuals, between different sites on the same individual, and within an individual over time. Skin includes stratified layers, a cellular epidermis, and an underlying dermis of connective tissue. Below the dermis is a subcutaneous fatty layer or adipose tissue. The epidermis is the thin outer layer that provides a barrier to infection and loss of moisture, while the dermis is the thick inner layer that provides mechanical strength and elasticity. The epidermis layer is 10 to 150 µm thick and is divided into three layers, the basal, middle, and superficial layers. The basal layer borders the dermis and contains pigment-forming melanocyte cells, keratinocyte cells, Langherhan cells and Merkel cells See F. Ebling, *The normal skin*, In: *Textbook of Dermatology*, A Rook, D. Wilkinson, F. Ebling, eds., 3ed., pp. 5-30, Blackwell Scientific Publishers, Oxford, England (1979). An outer superficial layer is also known as the stratum corneum.

The stratum corneum, the outermost layer of the mammalian epidermis, is formed and continuously replenished by the slow upward migration of aqueous keratinocyte cells from the germinative basal layer of the epidermis. It is replenished about every two weeks in mature adults. See W. Montagna, *The Structure and Function of Skin,* 2ed., p. 454, Academic Press, New York, (1961). This complex process involving intracellular dehydration and synthesis of an insoluble protein, keratin, results in keratin-filled, biologically inactive, shrunken cells. These flat, dehydrated, hexagonal cells are tightly bound to their neighbors and each is approximately 30 µm wide and 0.8 µm deep. See H. Baker, *The skin as a barrier*, In: *Textbook of Dermatology*, A. Rook, D. Wilkinson, F. Ebling, eds., 3ed., pp. 5 to 30, Blackwell Scientific Publishers, Oxford, England (1979). There are about twelve to twenty cell layers over most of the body surface. The stratum corneum is typically 10 to 20 µm thick, except on the planar surfaces, where it is considerably thicker. See A Kligman, *The*

*Biology of the stratum corneum,* in: *The Epidermis,* W. Montagna, W. Lobitz, eds. Academic Press, New York, pp. 387-433 (1964).

The major constituent of the dermis, apart from water, is a fibrous protein, collagen, which is embedded in a ground substance composed mainly of protein and glycosaminoglycans. The glycosaminoglycans play a key role in regulating the assembly of collagen fibrils and tissue permeability to water and other molecules. See K. Trier, S. Olsen, T. Ammitzboll, *Acta. Ophthalmol.,* v. 69, pp. 304 to 306 (1990). Collagen is the most abundant protein in the human body. Elastin fibers are also plentiful though they constitute a smaller proportion of the bulk. The dermis also contains other cellular constituents and has a very rich blood supply, though no vessels pass the dermo-epidermal junction. See Ebling, supra. The blood vessels nourish the skin and control body temperature. In humans, the thickness of the dermis ranges from 0.5 mm over the eyelid to 4 mm on the back and has an average thickness of approximately 1.2 mm over most of the body. See S. Wilson, V. Spence, *Phys. Med. Biol.* v. 33, pp. 894-897 (1988).

The spectral characteristics of water, protein, fat, urea, and glucose are all unique in the near-infrared from 1100 to 2500 nm.

Interaction Between Light and Human Skin

When a beam of light is directed onto the skin surface, a part of it is reflected while the remaining part penetrates into the skin. The proportion of reflected light energy is strongly dependent on the angle of incidence. At nearly perpendicular incidence, about 4% of the incident beam is reflected due to the change in refractive index between air ($\eta_D$=1.0) and dry stratum corneum ($\eta_D$=1.55). For normally incident radiation, this specular reflectance component may be as high as 7% because the very rigid and irregular surface of the stratum corneum produces off-normal angles of incidence. Regardless of skin color, specular reflectance of a nearly perpendicular beam from normal skin is between four percent and seven percent over the entire spectrum from 250 to 3000 nm. See R. Scheuplein, *J. Soc. Cosmet. Chem.,* v. 15, pp. 111 to 122 (1964). Only the air-stratum corneum border gives rise to a regular reflection. Indices of refraction of most soft tissue (skin, liver, heart, etc) lie within the 1.38 to 1.41 range with the exception of adipose tissue, which has a refractive index of approximately 1.46. See J. Parrish, R. Anderson, F. Urbach, D. Pitts, *UV-A: Biologic effects of ultraviolet radiation with emphasis on human responses to longwave ultraviolet,* New York, Plenum Press (1978). The differences are expected to be less significant when the stratum corneum is hydrated, owing to refractive index matching.

The 93 percent to 96 percent of the incident beam that enters the skin is attenuated due to absorption or scattering within any of the layers of the skin. These two processes taken together essentially determine the penetration of light into skin, as well as remittance of scattered light from the skin. A definition of diffuse reflectance or remittance is that fraction of incident optical radiation that is returned from a turbid sample. Absorption by the various skin constituents mentioned above account for the spectral extinction of the beam within each layer. Scattering is the primary process by which the beam is returned to the incident layer. Scattering results from differences in a medium's refractive index, corresponding to differences in the physical characteristics of the particles that make up the medium. The spatial distribution and intensity of scattered light depends upon the size and shape of the particles relative to the wavelength, and upon the difference in refractive index between the medium and the constituent particles.

The scattering coefficient of biological tissue depends on many uncontrollable factors, which include the concentration of interstitial water, the density of structural fibers, and the shapes and sizes of cellular structures. Scattering by collagen fibers is of major importance in determining the penetration of optical radiation within the dermis. See F. Bolin, L. Preuss, R. Taylor, R. Ference, *Appl. Opt,* v. 28, pp. 2297 to 2303 (1989). The greater the diffusing power of a medium, the greater the absorption related to multiple internal reflections. Therefore, reflectance values measured on different sites on the same person, or from the same site on different people, can differ substantially even when the target absorber is present in the same concentration. These differences are attributed to tissue parameters, such as gender, age, genetics, disease, and exogenous factors due to lifestyle differences. For example, it is known that skin thickness in humans is greater in males than females, whereas the subcutaneous fat thickness is greater in females. In another example, collagen density, the packing of fibrils in the dermis, is higher in the forearms of males than females. See S. Schuster, M. Black, E. McVitie, *Br. J. Dermatol, v.* 93, pp. 639 to 643, (1975).

Dynamic Properties of the Skin

While knowledge of and use of the properties of the skin, high instrument sensitivity, and compensation for inherent nonlinearities are all important for the application of noninvasive technologies to noninvasive tissue analyte measurements, an understanding of biological and chemical mechanisms that lead to time dependent changes in the properties of skin tissue is equally important and, yet, largely ignored. At a given measurement site, skin tissue is often assumed to be static except for changes in the target analyte and other interfering species. However, variations in the physiological state and fluid distribution of tissue profoundly affect the optical properties of tissue layers and compartments over a relatively short period of time. Such variations are often dominated by fluid compartment equalization through water shifts and are related to hydration levels and changes in blood analyte concentrations.

Total body water accounts for over 60% of the weight of the average person and is distributed between two major compartments: the intracellular fluid (two-thirds of total body water) and the extracellular fluid (one-third of total body water). See A. Guyton, J. Hall, *Textbook of Medical of Physiology, 9th* ed., Philadelphia, W.B. Saunders Company (1996). The extracellular fluid, in turn, is divided into the interstitial fluid, which is extravascular, and the blood plasma, which is intravascular. Water permeable lipid membranes separate the compartments and water is transferred rapidly between them through the process of diffusion to equalize the concentrations of water and other analytes across the membrane. The net water flux from one compartment to another constitutes the process of osmosis, and the amount of pressure required to prevent osmosis is termed the osmotic pressure. Under static physiological conditions the fluid compartments are at equilibrium. However, during a net fluid gain or loss as a result of water intake or loss, all compartments gain or lose water proportionally and maintain a constant relative volume.

An important mechanism for distributing substances contained in blood serum that are needed by the tissues, for example water and glucose, is through the process of diffusion. It is seen from Fick's Law that diffusion drives the short-term intra-/extra-vascular fluid compartment balance. The movement of water and other analytes from intravascular to extravascular compartments occurs rapidly as molecules of water and other constituents, including glucose, in constant thermal motion, diffuse back and forth through the capillary wall. On average, the rate at which water molecules diffuse through the capillary membrane is about eighty times greater than the rate at which the plasma itself flows linearly along the capillary. In the Fick's Law expression, the actual diffusion flux, $I_{OA}$, is proportional to the concentration gradient, $dC/dx$ between the two compartments and the diffusivity of the molecule, $D_A$ according to the equation $$I_{OA} = D_A]\frac{dC}{dx} \quad (1)$$

Short-term increases (or decreases) in blood glucose concentrations lead to an increase (or decrease) in blood osmolality (number of molecules per unit mass of water). Fluid is rapidly re-distributed accordingly and results in a change in the water concentration of each body compartment. In the case of hyperglycemia, the osmotic effect leads to a movement of extravascular water to the intravascular space compartment where glucose concentrations are higher. At the same time, glucose is transported from the intravascular space to the extravascular compartment in an effort to equilibrate the osmolality of the two compartments. Conversely, a decrease in blood glucose concentration leads to a movement of water to extravascular space from the intravascular compartment, along with the movement of glucose from the extravascular space into the intravascular space.

Because the cell membrane is relatively impermeable to most solutes but highly permeable to water, whenever there is a higher concentration of a solute on one side of the cell membrane, water diffuses across the membrane toward the region of higher solute concentration. Large osmotic pressures can develop across the cell membrane with relatively small changes in the concentration of solutes in the extracellular fluid. As a result, relatively small changes in concentration of impermeable solutes in the extracellular fluid, such as glucose, can cause tremendous changes in cell volume.

Sampling Error

Noninvasive measurement of tissue properties and analytes, such as blood glucose concentration, may employ near-infrared (near-IR) spectroscopic methods. S. Malin, T. Ruchti, supra, describes a system for noninvasively estimating blood glucose concentrations in-vivo, using near-infrared spectral analysis. Such near-infrared spectroscopy-based methods use calibrations that are developed using repeated in-vivo optical samples of the same tissue volume. Repeatability of these successive measurements is needed to produce a usable calibration. As herein described, the heterogeneous and dynamic nature of living human skin leads to sampling uncertainty in the in-vivo measurement. Sampling differences can arise due to variable chemical composition and light scattering properties in tissue. As an example: because glucose is not uniformly distributed in tissue, a variation in the volume of tissue sampled is likely to lead to a variation in the strength of the glucose signal, even though glucose concentration in the tissue or blood remains constant.

Variation in the repeated placement of the optical probe used for sampling at the measuring surface site can lead to sampling errors in two separate ways. First, variations in the location of the probe can cause a different tissue volume to be sampled and, second, varying the amount of pressure applied by the probe on the tissue can alter the optical scattering by the tissue, thereby changing the sampled tissue volume. A change in optical sampling may lead to a variation in the spectral signal for a target analyte, even though the concentration of the analyte in the blood or tissue remains unchanged. Furthermore, air gaps between the surface of the optical probe and the surface of the tissue being sampled give rise to variable surface reflection. Variable surface reflection leads to a variable light launch into the tissue that, in turn, gives rise to an increase in nonlinear nature of the spectral measurements. Certainly, a variable nonlinear measurement is difficult to calibrate.

Various systems for guiding and coupling optical probes are known. For example, M. Rondeau, High precision fiber optic alignment spring receptacle and fiber optic probe, U.S. Pat. No. 5,548,674 (Aug. 20, 1996) and R. Rickenbach and R. Boyer, Fiber Optic Probe, U.S. Pat. No. 5,661,843 (Aug. 26, 1997) both disclose fiber optic probe guides using ferrules through which a fiber optic cable or thread is longitudinally threaded. Both devices are connectors that couple fiber optic cables or threads to receptacles in various forms of medical equipment, or to other fiber optic cables. Neither device provides a means for repeatably coupling a fiber optic probe to a tissue measurement site.

T. Kordis, J. Jackson, and J. Lasersohn, Systems using guide sheaths for introducing, deploying and stabilizing cardiac mapping and ablation probes, U.S. Pat. No. 5,636,634 (Jun. 10, 1997) describe a system that employs catheters and guide sheaths to guide cardiac mapping and ablation probes into the chambers of the heart during surgery or diagnostic procedures. The Kordis teachings are directed to surgical methods for the heart, and have nothing to do with optical sampling of tissue in-vivo. Furthermore, the apparatus of Kordis et al. is not suitable for repeatably coupling an optical probe to a tissue measurement site.

M. Kanne, Laser mount positioning device and method of using the same, U.S. Pat. No. 5,956,150 (Sep. 21, 1999) describes a method for using an illumination device, such as a laser to align two components during an assembly process. The Kanne teachings are directed to a manufacturing process rather than optical sampling of tissue in-vivo. The Kanne device does not provide any means for repeatably placing a probe guide at a tissue measurement site. It also lacks means for monitoring the surface temperature at a tissue measurement site and for minimizing surface temperature fluctuations and accumulation of moisture at a tissue measurement site.

D. Kittell, G. Hayes, and P. DeGroot, Apparatus for coupling an optical fiber to a structure at a desired angle, U.S. Pat. No. 5,448,662 (Sep. 5, 1995) disclose an optical fiber support that is coupled to a frame for positioning an optical fiber at a desired angular position. As with the prior art previously described, the teachings of Kittell et al. have nothing to do with optical sampling of tissue in-vivo. Furthermore, the disclosed device allows an operator to immobilize an optical fiber so that it is maintained in a fixed position, but it lacks means of repeatably coupling a fiber optic probe to a tissue measurement site. It also has lacks means for monitoring the surface temperature at a tissue measurement site and for minimizing accumulated moisture and temperature fluctuations at the site.

R. Messerschmidt, Method for non-invasive blood analyte measurement with improved optical interface, U.S. Pat. No. 5,655,530 (Aug. 12, 1997) discloses an index-matching medium to improve the interface between a sensor probe and a skin surface during spectrographic analysis. Messerschmidt teaches a medium containing perfluorocarbons and chlorofluorocarbons. Because they are known carcinogens, chlorofluorocarbons (CFC's) are unsuitable for use in preparations to be used on living tissue. Furthermore, use of CFC's poses a well-known environmental risk. Additionally, Messerschmidt's interface medium is formulated with substances that are likely to leave artifacts in spectroscopic measurements.

E. Ashibe, Measuring condition setting jig, measuring condition setting method and biological measuring system, U.S. Pat. No. 6,381,489 (Apr. 30, 2002) describes a measurement condition setting fixture secured to a measurement site, such as a living body, prior to measurement. At time of measurement, a light irradiating section and light receiving section of a measuring optical system are attached to the setting fixture to attach the measurement site to the optical system. Ashibe does not describe a flexible jig, a two part jig, a jig with a flexible component, or a jig with movable parts. Further, Ashibe does not describe rotational control of a sample probe relative to the sample for a symmetrical or one piece probe tip.

There exists, therefore, a need in the art for a means of achieving the precise optical sampling necessary for developing noninvasive calibrations for measuring tissue analytes.

A solution to the problem of controlling optical sampling during a noninvasive measurement must address several challenges posed by the structural characteristics and dynamic properties of living tissue, such as:

Controlling surface reflection due to optical aberrations in surface coupling and stretching of the surface tissue;

Controlling variations in tissue volume sampled due to imprecise placement;

Controlling variable stretching of dermal collagen, leading to sampling volume uncertainty;

Correcting measurement bias related to water pooling in the tissue resulting from pressure on the area in the vicinity of the measurement site from instrumentation or placement guides; and Stabilizing hydration of surface tissue.

It is desirable to provide:

A placement guide for an optical probe that couples the probe to a tissue measurement site for in-vivo optical sampling of the tissue in a fashion allowing increased precision and accuracy of noninvasive analyte concentration estimations;

A means of assuring that the same tissue sample volume is repeatably sampled, thus eliminating sampling errors due to mechanical tissue distortion and probe placement;

A way to minimize temperature fluctuations and stabilize stratum corneum moisture content at the tissue measurement site, thus eliminating further sources of sampling error;

An optical coupling medium to provide a constant interface between an optical probe and the skin at a tissue measurement site that is non-toxic and non-irritating and that does not introduce error into spectroscopic measurements;

A means of monitoring surface temperature at the tissue measurement site, therefore assuring that the temperature remains constant across repeated optical samples; and A means for correcting the tissue sampling bias that results from the uncertainty inherent to the mechanical attachment process used to install the placement guide at the measurement site.

Currently, no device using near-infrared spectroscopy for the noninvasive measurement of glucose is in use by persons with diabetes due to technology limitations that include sampling problems, calibration bias, short and long-term reproducibility, and stability. Further, current reported versions of noninvasive glucose concentration analyzers do not consistently yield accurate estimations of glucose concentrations in long-term patient trials in the hands of a typical user or professional operator due, in part, to usability issues. There exists, therefore, a long-felt need for a noninvasive approach to the estimation of glucose concentration that provides long-term accurate and precise glucose concentration estimations in a semi-continuous fashion. Therefore, it is of great benefit to simplify the sampling process and to add controls that enhance precision and accuracy of glucose concentration estimations in the hands of a lay user or professional. Clearly, a guide would be beneficial to a noninvasive optical measuring system allowing tighter control of the sampling and environmental conditions.

SUMMARY OF THE INVENTION

The invention provides an optical sampling interface system that minimizes sampling variation and/or state fluctuations at a measurement site, thereby allowing optical tissue sampling and subsequent noninvasive analyte concentration estimation with increased precision and accuracy.

DETAILED DESCRIPTION OF THE INVENTION

Figure 1:
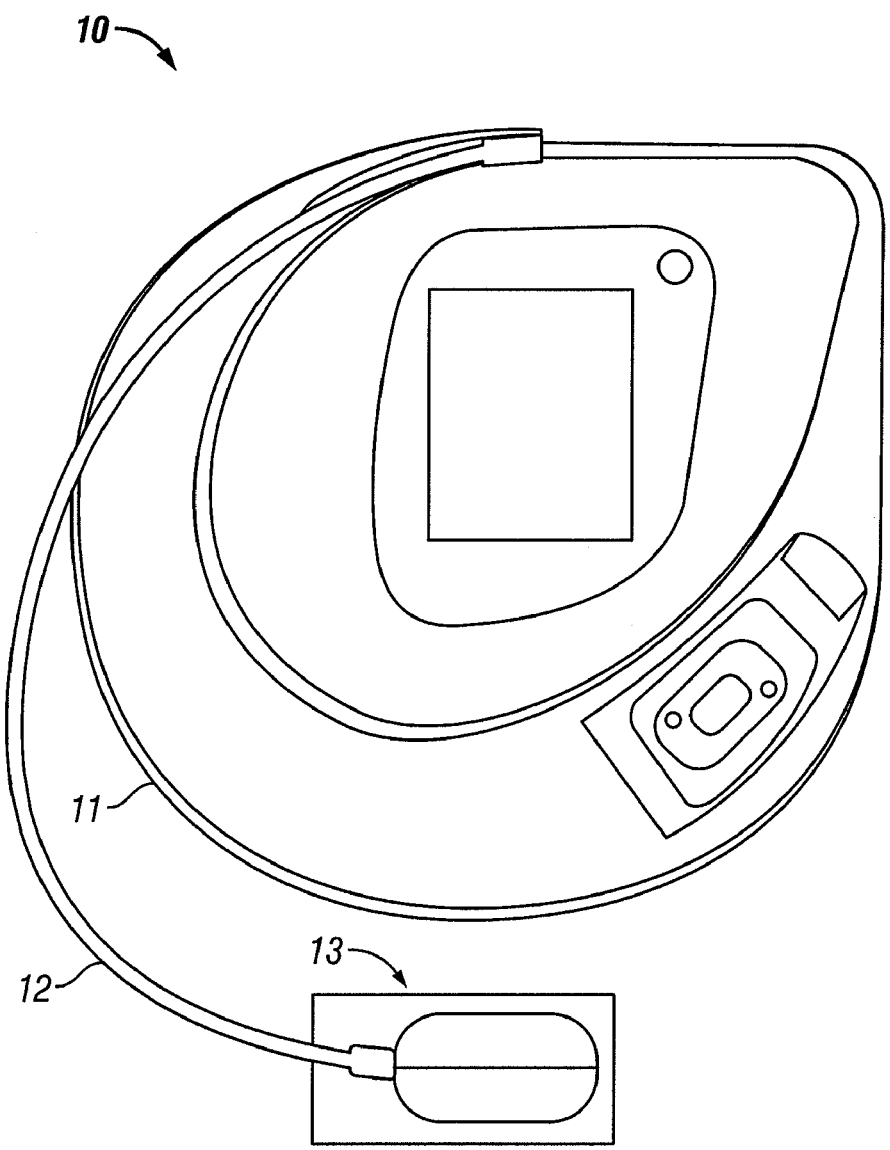
FIG. 1 is a perspective view of a glucose tracking system analyzer according to the invention.

The following detailed description should be read with reference to the drawings in which similar elements in different drawings are numbered the same. The drawings, which are not necessarily to scale, depict illustrative embodiments that are not intended to limit the scope of the invention.

In spectroscopic analysis of living tissue, it is often necessary to sample optically the same tissue volume repeatedly through the use of an optical probe for example while developing a noninvasive calibration for measuring one or more tissue analytes, and/or subsequently, when taking measurements for the actual analyte concentration estimation. Sampling errors can be introduced into these measurements because of the difficulty of repeatedly placing the optical probe at the precise location used in preceding measurements, and repeatably producing the same nominal degree of tissue distortion and displacement. With each small variation in the location of the probe, or variations in the amount of pressure resulting from the repeated probe contact events, a slightly different tissue volume is sampled, thereby introducing sampling errors into the measurements. The invention provides an optical sampling interface system, jig, or guide that eliminates or minimizes factors that account for sampling error. An optical probe placement guide facilitates repeatable placement of an interfacing optic, such as an optical sample probe tip, with the surface of a tissue measurement site with a minimal degree of tissue distortion and displacement. Repeatable placement is also described as indexing a position or registering a position.

The major structural component of a probe placement guide is a mechanical interface of one or more guide elements with one or more corresponding sections of the interfacing sample probe. The lock and key mechanism of the guide element(s) and the interfacing sample probe improves the precision of probe placement during the course of multiple measurements. Different embodiments of the invention include a guide comprising any of:

A single part of the guide that controls the sample probe position relative to the tissue sample site for any of:
  an x-position;
  a y-position;
  a z-position; and
  a rotational position;
At least one section of the guide that is flexible; and
At least two separate parts of the guide wherein the two elements control alignment of the sample probe relative to a tissue sample site.

Embodiments of the invention use a guide that does at least one of:
Induces the formation of a tissue meniscus, created by the pooling of epidermal water in the guide aperture due to the relative difference in the contact pressure at the guide adhesion surface and the guide aperture, where no part of the guide contacts the tissue;
Minimizes interference due to surface irregularities and controls variation in the volume of tissue sampled;
Uses a two-part guide system;
Uses a guide that controls rotation of a sample probe and allows z-axis movement of the probe;
Uses a separate base module and sample module in conjunction with a guide;
Uses a guide that controls rotation;
Uses a guide with at least one flexible part; and
Uses a guide of two or more layers.

An optional occlusive element placed over the tissue meniscus isolates the tissue meniscus from environmental fluctuations. The occlusive element stabilizes and controls the temperature of the surface of the sample site and/or stabilizes the degree of hydration of the tissue meniscus and thereby stabilizes surface tension of the tissue meniscus.

An optional coupling medium placed on the surface tissue at the tissue measurement site eliminates sampling errors due to air gaps between the skin surface and the optical probe.

An optional measurement and bias correction element applies a bias correction to spectral measurements, and the associated analyte measurement. Precision in sampling location allows bias to be removed if a correction process, such as mean centering, is used in the algorithm. This is addressed in the preprocessing section below. Such bias corrections are performed for example, with all data taken over the course of one guide placement or until another reference concentration is determined. When the guide is removed and replaced, a new bias correction is preferably determined for all subsequent data taken with the second guide placement.

Additionally, each of the separate elements of the invented system can be individually deployed as standalone solutions to counter various sources of measurement error. Thus, the probe placement guide, independent of the other elements of the system, provides a significant reduction in sampling error. The occlusive element provides a significant reduction in measurement error due to state fluctuations at the surface of the measurement site. The correction algorithm can be applied to spectral measurements in settings lacking the other elements of the system. Each of these separate elements are further described, infra.

Instrumentation

An analyte detection and/or concentration tracking system is used, such as a glucose tracking system. Referring now to FIG. 1, an example of a glucose concentration tracking system (GTS) is presented. The system uses a glucose concentration analyzer that comprises at least a source, a sample interface, at least one detector, and, a system for implementing an associated algorithm. In FIG. 1, an analyzer 10 is separated into elements including a base module 11, a communication bundle 12, and a sample module 13. The advantages of separate units are hereinafter described. The sample module, also referred to as a sampling module, interfaces with a tissue sample and at the same or different times with one or more reference materials. Herein, the combined base module 11, communication bundle 12, sample module 13, and system for implementing the algorithm are referred to as a spectrometer and/or analyzer 10. Preferably, the base module and sample module are in separate housings. Providing separate housings for the sample module and base module has multiple benefits, such as thermal, size, and weight management. For example, the sample module is allowed to be smaller and weigh less without the bulk of the base module. This allows easier handling by the user and less of a physical impact on the sample site by the sample module. In a further example, heat from a source in one housing is separated from a detector in a second housing, allowing for ease in cooling the detectors, thereby resulting in lower detector noise. The sample module, base module, and communication bundle are further described, infra. Alternatively, all of the components of a noninvasive glucose analyzer are included in a single unit, such as a professional use analyzer, a stand-alone analyzer, or a handheld analyzer.

Sample Module

The sample module includes a sensor head assembly that provides an interface between the glucose concentration tracking system and the patient. The tip of the sample probe of the sample module is brought into contact with the tissue sample. Optionally, the tip of the sample probe is interfaced to a guide, such as an arm-mounted guide, to conduct data collection and removed when the process is complete. Guide accessories include an occlusion plug that is used to fill the guide cavity when the sensor head is not inserted in the guide, and/or to provide photo-stimulation for circulation enhancement. In one example, the following components are included in the sample module sensor head assembly: a light source, a single fiber optic, and coupling fluid. Preferably, the sample module is in a separate housing from the base module.

Alternatively, the sample module is integrated into a single unit with the base module, such as in a handheld or desktop analyzer. In this alternative embodiment, the communication bundle is wireless or is integrated into the analyzer, Communication Bundle The communication bundle is a multi-purpose bundle. The multi-purpose bundle comprises a flexible sheath that comprises at least one of:

Electrical wires to supply operating power to the lamp in the light source;
Thermistor wires;
One or more fiber-optics, which direct diffusely reflected near-infrared light to the spectrograph;
A tube, used to transport optical coupling fluid from the base unit, through the sensor head, and onto the measurement site;
A tension member to remove loads on the wiring and fiber-optic strand from pulls; and
Photo sensor wires.

Preferably, the analyzer is packaged with labeling instructions to train the user not to twist the bundle and, optionally, mechanical means to prevent the bundle from twisting more than one-quarter turn in either direction.

Base Module

A signal is communicated from the sample module to a base module. Preferably, a portion of the diffusely reflected light from the site is collected and transferred via at least one fiber-optic, free space optics, digitally after detection, or via an optical pathway to the base module. Preferably, the base module contains a spectrograph. The spectrograph separates the spectral components of the diffusely reflected light, which are then directed to the photo-diode array (PDA). The PDA converts the sampled light into a corresponding analog electrical signal, which is then conditioned by the analog front-end (AFE) circuitry. The analog electrical signals are converted into their digital equivalents by the analog circuitry. The digital data are then sent to the digital circuitry where they are checked for validity, processed, and stored in non-volatile memory. Optionally, the processed results are recalled when the session is complete and, after additional processing, the individual glucose concentrations are available for display or transfer to a personal computer. The base module also, preferably, includes a central processing unit or equivalent for processors, memory, storage media for storing data, a model, a multivariate model, and/or analysis routines, such as those employing a model or net analyte signal.

Probe Placement Guide

A system is described herein that provides superior sampling precision of the target tissue volume through the use an optical probe placement guide or jig that is removably attached to the tissue site to achieve the goal of highly repeatable sample probe placement at a targeted tissue measurement site. A key characteristic of the guide is that it provides a means for registering the location of the targeted tissue volume with respect to the optical probe and/or tip of a sample module, such that a particular tissue volume is precisely sampled by the optical system. Registration refers to providing feedback regarding the position of the optical probe relative to a target location on the tissue. The means for registering between the guide and the optical probe may be mechanical, optical, electrical, and/or magnetic. Additionally, some embodiments of the invention allow for a more constant pressure/constant displacement to be applied to the sampling location which also enhances precision and accuracy of the glucose determination. While the guide greatly enhances positioning and allows associated data processing to be simpler and more robust, the guide is not an absolute requirement of the sampling module.

A number of embodiments of the invention are described, infra. Additional embodiments are envisioned that are permutations and combinations of guide components and/or accessories of the various described embodiments.

Herein, an x, y, and z coordinate system relative to given a body part is used. The x-axis is along a body part, such as from an elbow to the wrist, from the shoulder to the elbow, or along the length of a digit of a hand. The y-axis moves across a body part. Together, the x, y plane tangentially touches the skin surface, such as at a sample site. The z-axis is normal to the x, y plane, such that an object moving toward the skin surface is moving along the z-axis. Thus a sample probe brought toward a sample site is moving along roughly the z-axis.

Figure 2:
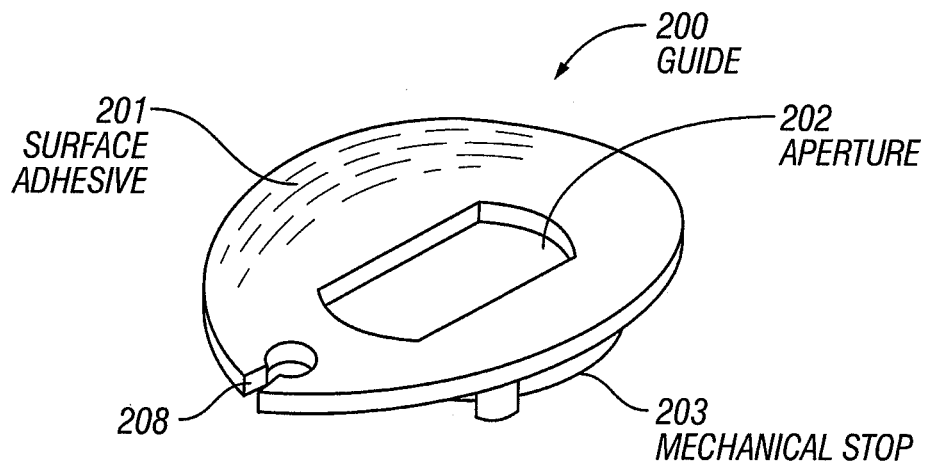
FIG. 2 shows an optical probe placement guide according to the invention.

A first embodiment of the invention comprises a guide 200, having an aperture 202, a mechanical stop 203, and an optional temperature probe opening or slot 208. Referring now to FIG. 2, an example of the first embodiment of a guide 200 is provided. In this embodiment, the guide at least partially surrounds an interfacing optic for the purpose of sampling in a precise location. Typically, this is done with an interface with defined points that interface part of the sample module, such as the sample probe in a lock and key fashion.

The guide 200, optionally, is provided in a number of shapes. An oval outer perimeter of a guide is shown in FIG. 2. Additional shapes of the outer perimeter include a number of geometric shapes, such as rectangular, oval, circular, elongated, curved, or polygon. Preferably, the outer edge of the guide is beveled to prevent snagging, such as by loose clothing or by an outside object, such as a tabletop or arm support. In addition, the outer edge of the guide on the outer surface, away from the sample site, is preferably rounded or beveled to reduce weight. Preferably, the outer shape presented in FIG. 2 approximates the surface of the sampled tissue site, for example, an oval guide is used with the volar or dorsal surface of the forearm. However, other shapes are used for other locations of the body such as the hand, the earlobe, the leg, the abdomen, the upper arm region, and the fingers.

In the first embodiment, the guide comprises an aperture into which the optical probe is received. The guide has an aperture 202, into which an optical probe is received. The sizes and shapes of the optical probe and the guide aperture 202 are matched to each other such that when the optical probe is received by the guide, it fits snugly and provides a mechanical registration in the x-y plane relative to the tissue measurement site. The aperture serves several purposes including at least one of:

A mechanical registration point;
A means for creating a stable tissue meniscus; and
An opening for receiving an occlusion plug so that the surface state of the tissue at the measurement site may be stabilized between measurements.

To avoid over-penetration of the optical probe into the tissue, and to promote a repeatable pressure between the optical probe and the tissue, the guide and the optical probe are equipped with mechanical stops 203 that limit and control the penetration of the optical probe into the tissue (the z-direction). The weight of the tissue is transferred to the optical probe through the mechanical stop 203. The weight is preferably distributed across the guide, as opposed to being on the sample site surface, thereby reducing the pressure at the tissue measurement site. Optionally, a flexible material or movable wings with some resistance are used to cushion the weight or distribute the weight of the sample probe, respectively. Guides with flexible materials are further described, infra.

In multiple embodiments of the invention, the guide is, optionally, equipped with an opening 208 for the optional insertion of a temperature probe. This feature is particularly useful during the calibration phase for monitoring of skin temperature.

In multiple embodiments of the invention, the analyzer or sample module couples with a guide that is semi-permanently attached to the skin with a replaceable adhesive layer 201. The adhesive layer 201 resides between the inner surface of the guide 200 and the region about the sample site. In a first example, the adhesive layer is applied to the guide at the time of manufacture. Optionally, the adhesive layer is applied to the guide or tissue sample prior to usage. Generally, the adhesive covers the entire inner surface of the guide, that surface of the guide that is in contact with the skin area adjacent to and surrounding the tissue measurement site. Additionally, other attachment means are suitable such as straps, suction, or armbands.

The guide is attached to the tissue site at the beginning of a measurement period or some time before the beginning of a measurement period, infra. In multiple embodiments of the invention, the guide is attached to the subject for a period of time, such as the waking hours of the subject. Typically, this period is the beginning of a particular day after a previously used guide has been removed. The guide is alternatively attached for a shorter time period or in a more permanent fashion, such as for a day, week, or month, especially in continuous monitoring glucose analyzers discussed below. In the preferred embodiment, the method of attachment is to place the guide 200 onto a noninvasive measurement device with the adhesive layer in place and exposed. The tissue measurement site is then placed onto the guide. During this first placement, the guide becomes affixed to the tissue site.

In multiple embodiments of the invention, the curvature of the guide surface contacting the tissue sample is a shape correlating to the tissue. For example, on a relatively flat portion of the body, such as the abdominal region or thigh, the inner surface or tissue side of the guide is preferably flat or nearly flat. In a second example, on a region of the body with intermediate curvature, such as an arm, the inner surface of the guide has a curvature that complements the region of curvature about the sample, such as a radius of curvature of about 6, 4.5, 3, or 1.5 inches. In a third example, on a region of the body with tight curvature, such as a fingertip, the inner surface of the guide has a curvature that complements the region of curvature about the sample, such as a radius of curvature of about 0.6, 0.4 or 0.2 inches.

The design of a guide is intended to allow for comfortable and unobtrusive use without application of significant mechanical energy to the sampled tissue site. The guide 200 allows for the distribution of mechanical energy transferred from the instrument to the arm over a greater area around the measurement site. For example, a guide is composed of a rigid polymer, allowing for the creation of a stable tissue meniscus. In another example, in applications involving a portion of the body subject to deformation or movement, the guide is composed of a flexible material, such as a flexible polymer, that provides for a stabilization of the measurement site and deformation of the underlying tissue without applying undue force to the targeted tissue volume. A flexible material, such as SORBOTHANE™ (Sorbothane Inc., Kent, Ohio), allows for reduced tissue distortions as the guide flexes on the surface of the sample rather than pushing into the sample. In a third example, the guide is partially made of a rigid material and partially made of a flexible material, such as having rigid elements for alignment and flexible elements for distribution of applied forces from the sample probe. Other materials providing the requisite combination of rigidity and light weight, such as lightweight metals, are also suitable.

Figure 3:
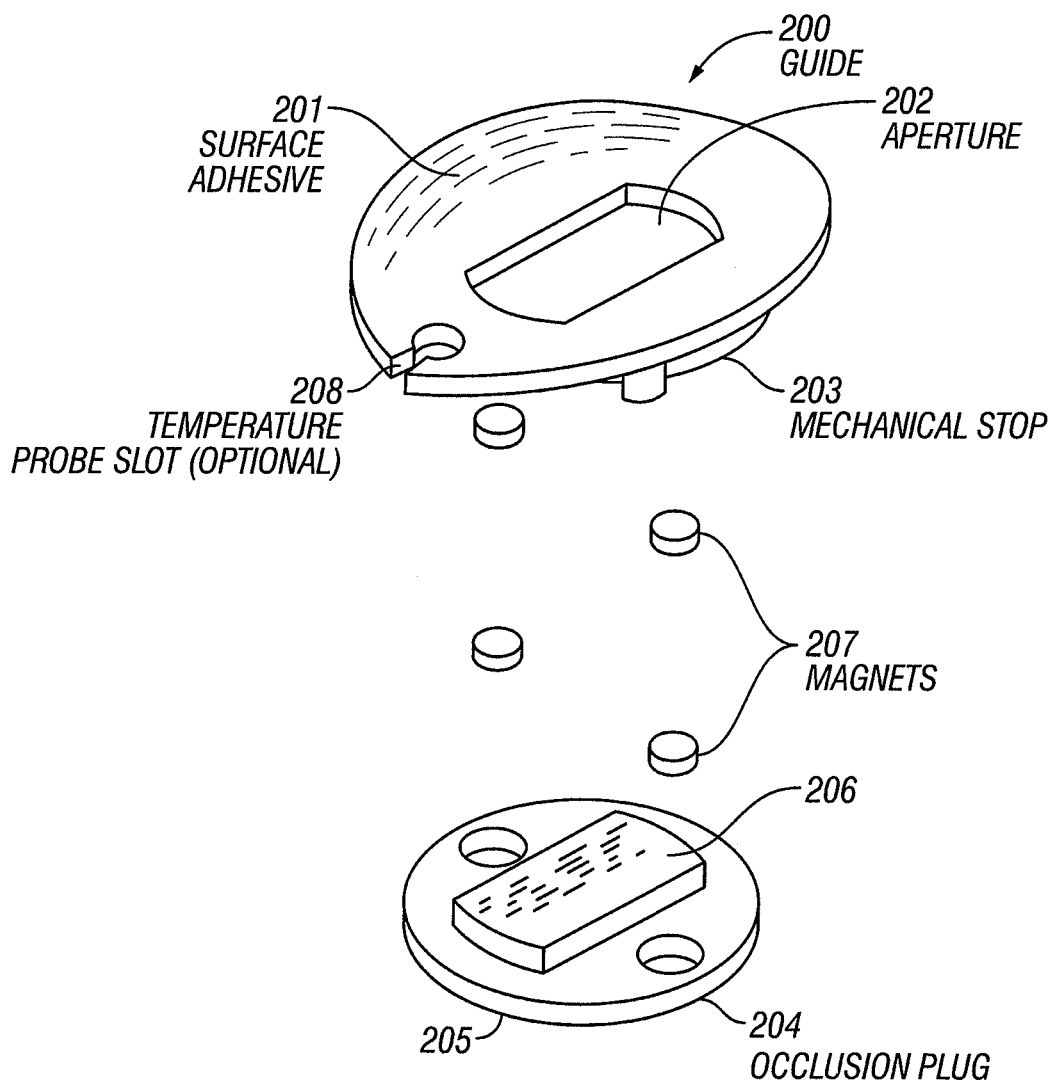
FIG. 3 provides a sample probe placement guide that uses a magnet according to the invention.

A second embodiment of the invention uses magnets to align a portion of a sample module to a sample site precisely and replaceably. Referring now to FIG. 3, an example of magnets 207 placed into a guide 200 and a device coupled to the guide is provided. In this case, a plug 204 is pictured that has magnets corresponding to the magnets of the guide. Alternatively, the sample module and/or one or more reference materials have magnets that correspond to the guide magnets.

Magnets are used for at least one of:
  Aiding, in a user friendly mechanism, coupling of the tip of the sampling module to the sample site;
  Reversibly attaching a module, such as a plug, sample probe, and/or reference to the guide;
  Aiding in providing a pulling force, such that the optical probe is pulled into the guide aperture; and
  Allowing a constant, known, and precise alignment between the sample probe and the sampled site.

In the preferred embodiment two magnets are used, one on each side of the sampled site, to enhance alignment. One magnet coupled to a magnetizable material or a larger number of magnets are alternatively used to provide the same effect. Alternatively, one or more magnets are electrically activated to facilitate a controlled movement of the probe into the guide aperture and to allow, through reversal of the magnet poles, the probe to be withdrawn from the guide without pulling on the guide. It is recognized that there exist a large number of alternative mechanical methods for coupling two devices together, such as lock and key mechanisms, electro-magnets, machined fits, VELCRO, adhesives, snaps, and many other related techniques commonly known to those skilled in the art.

A third embodiment provides a cover in the aperture of a guide, such as a window, a longpass filter, or a bandpass filter. A window, such as an optical window, allows light to penetrate through the guide while still providing control of the surface of the sample site, such as occlusion and temperature control of the sample site. Alternatively, the aperture houses a removable plug. The contact of a window or plug with the skin stabilizes the tissue by providing the same tissue displacement as the probe and increases the localized skin surface and shallow depth hydration. As opposed to the use of a removable plug, use of a contact window allows a continuous barrier for proper hydration of the sampling site and a constant pressure interface. The use of a plug or contact window leads to increased precision and accuracy in glucose determination by the removal of issues associated with dry or pocketed skin at the sampling site.

A fourth embodiment uses a guide that controls rotational freedom of a sample probe relative to the sample site. Rotational freedom is controlled using means that orient the sample probe in a certain direction relative to the guide, such as mechanical, electrical, or magnetic means. A first half of a lock and key mechanism is on the guide and the corresponding half of a lock and key mechanism is on the sample probe. For example, the guide contains a mechanical extrusion, such as an isosceles triangle shaped post or a post or indentation with a single rotational degree of freedom, an indentation, or stop that limits the rotational orientation of the corresponding probe part. In a second example, a magnet, such as a rod, is placed into the guide with a north and south pole. A corresponding magnet, such as a matching rod, is placed into the sample probe with a north and south pole in the opposite orientation. When the guide and sample probe are brought together, the opposite poles attract the two pieces together into an aligned orientation.

Controlling the x-, y-, and z-position of a part does not necessarily control the rotational position of a part. For example, a top stays in the same x-, y, and z-position while spinning, yet the rotation varies. In the language of symmetry and rotation, unlimited rotation $C_x$ is different from $C_N$ where N is an integer from 1 to less than infinity. In the case of a sample module and/or communication bundle, controlling the rotation of the interfacing sample module or communication bundle, is important and is not controlled by x-, y-, and z-positioning of the items relative to the guide.

Controlling rotation of the sample probe is important for a number of reasons. First, photons are not evenly distributed across a cross-section of the optical path in most optically-based instruments. Typically, hot spots exist that have a larger photon flux compared to other regions of the cross-section. For example, the incident photons from the source of a sample module are not evenly distributed without additional optics or great care and expense in alignment. In the instance where a collection fiber crossed the optical path of the incident photons, a shadow is created that creates a cool spot in the cross sectional profile of the incident optics. In a module where the cross sectional photons are not evenly distributed, rotation of the sample module interface moves the hot spot on the sampled tissue. Because tissue is not homogenous, this results in a sample spectrum that varies with rotation. Second, an incident optic and/or a collection optic is often physically attached to an additional part. For example a source fiber is attached to a mount and a collection fiber is attached to a slit. Rotation of the sample module causes rotation of the optics, such as a fiber optic. In the case of a fiber optic, rotation results in micro-cracking of the core of the fiber or of the cladding about the fiber. This results in lost photons and an imprecise reading with rotation. Third, interfacing optics are not necessarily symmetrical. For example, a sampling probe comprised of an excitation fiber and a collection fiber is not symmetrical. Similarly, a separate sample probe and collection probe on the same side of a tissue sample and necessarily not symmetric. Therefore, rotation of the probe results in sampling different tissue volumes with rotation. From these three examples, it is observed that rotational control allows at least more flexibility in probe design and/or increased precision in sampling.

Figure 4:
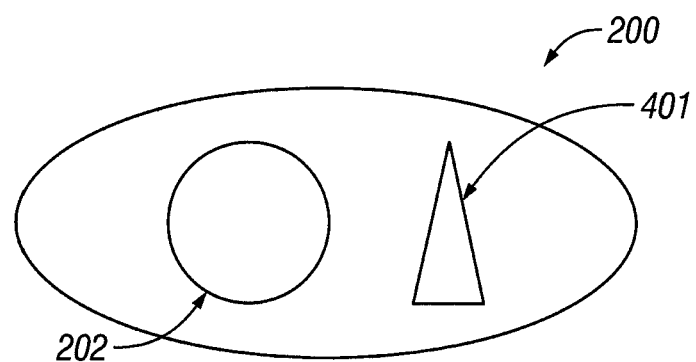
FIG. 4 shows a jig for sample probe registration that includes a rotational alignment control according to the invention.

Referring now to FIG. 4, an example of a guide 200 with a mechanical registration piece 401 is presented. The mechanical registration piece 401 limits rotational freedom of the corresponding part of a sample probe to a single orientation. In this example, the tissue sample site 402 is accessed through an aperture 202 that is contained within the guide. The x- and y-position of the sample probe is controlled relative to the guide and tissue sample site in an instance where the sample probe outer dimensions are tightly controlled to the aperture size.

An additional benefit of controlling rotational freedom is that one or more of the x-, y-, and z-positions of the sample probe are set while aligning the rotational orientation of the sample probe relative to the guide. For example, a magnet flush with the surface aligns at least the z-position or a corresponding sample probe that also has a magnet flush with the surface. In a second example, an extrusion from the guide or an indentation into the guide align the corresponding indentation or extrusion of a sample probe in one or more of the x-, y-, and z-positions.

Depending upon the guide 200 sample probe design, the tissue sample site 402 is, optionally, in a region that is sampled through an aperture in a guide, in a region that is outside of the contact area of the guide with the sample, or is in a region partially within the guide.

Figure 5:
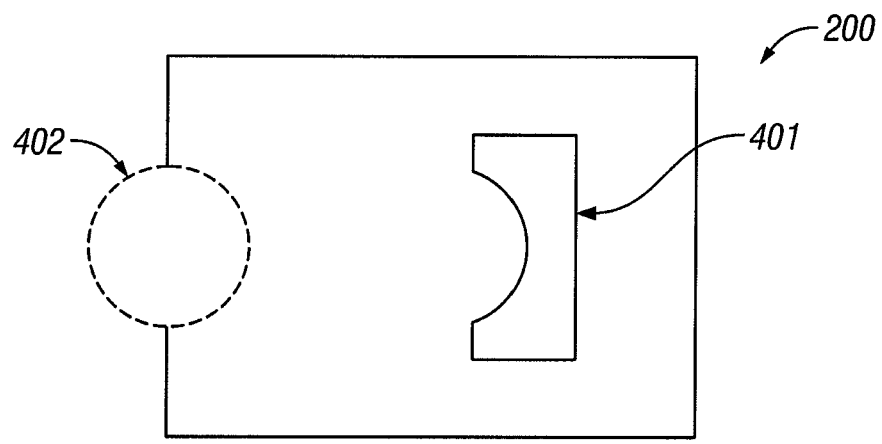
FIG. 5 illustrates a guide for alignment of a sample probe to a tissue site with an aperture partially within the perimeter of the guide according to the invention.

Referring now to FIG. 5, an example of a polygonal guide 200 with a polygonal mechanical registration piece 401 is presented, where the sample site is partially overlapping with the generic shape of the guide. The corresponding sample probe has a tip that has a shape and or dimension that is different from the guide. At least the part of the sample probe that aligns to the registration piece 401 is complementary to the guide. A separate section of the sample probe controls the incident and/or collection photons to a sample region 402 partially contained by the boundary of the guide. The mechanical registration piece in this example controls the rotational orientation of the sample probe. In the instance where the registration piece is formed in three-dimensions and corresponds to a matching piece on the sample probe, the x-, y-, and z-position of the sample probe is also controlled versus the sample site.

Figure 6:
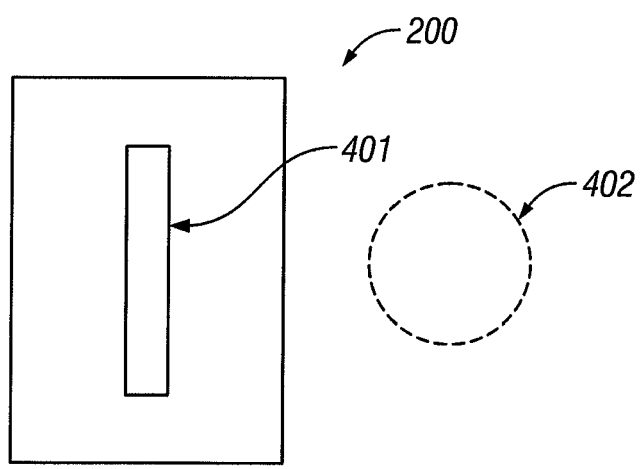
FIG. 6 illustrates a guide for alignment of a sample probe to a tissue site with an aperture outside the perimeter of the guide according to the invention.

Referring now to FIG. 6, an example of a rectangular guide 200 with a magnetic registration piece 401 is presented where the sample site is outside of the region of the guide. The magnetic registration piece in this example controls the rotational orientation of the sample probe through the magnetic alignment of the poles, as described heretofore. A separate section of the sample probe controls the incident and/or collection photons to a sample region 402 outside the perimeter of the guide footprint. In the instance where the magnetic pieces of both the guide and corresponding sample probe are flush with their respective surface, the registration piece controls the z-position of the sample probe relative to the sample site.

Figure 7:
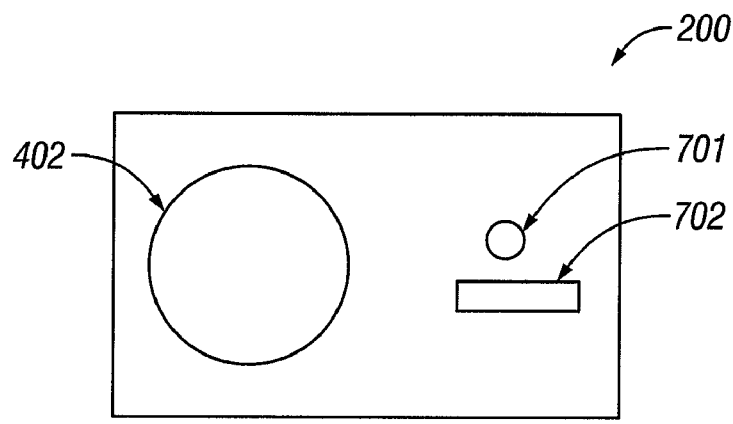
FIG. 7 illustrates a guide with two registration points for control of at least rotational alignment according to the invention.

A fifth embodiment of the invention includes a guide with at least two registration pieces. Referring now to FIG. 7, a guide 200 is presented that has a first registration piece 701 and a second registration piece 702. Combined, the two registration pieces on the guide control at least one of the x-, y-, and z-position, as well as the rotational alignment of the corresponding sample probe. In the example presented in FIG. 7, the first alignment piece controls at least the x-position and y-position of the sample probe and the second alignment piece controls the z-position. Combined, the two alignment pieces control the rotational alignment of the sample probe. Many combinations exist where the first registration piece and second registration piece each control one or more of the x-position, y-position, z-position, and rotational alignment of the sample probe. In the broadest sense of this embodiment, the first and second registration pieces combined control any of the x-position, y-position, z-position, and rotational alignment of the corresponding sample probe.

Figure 8:
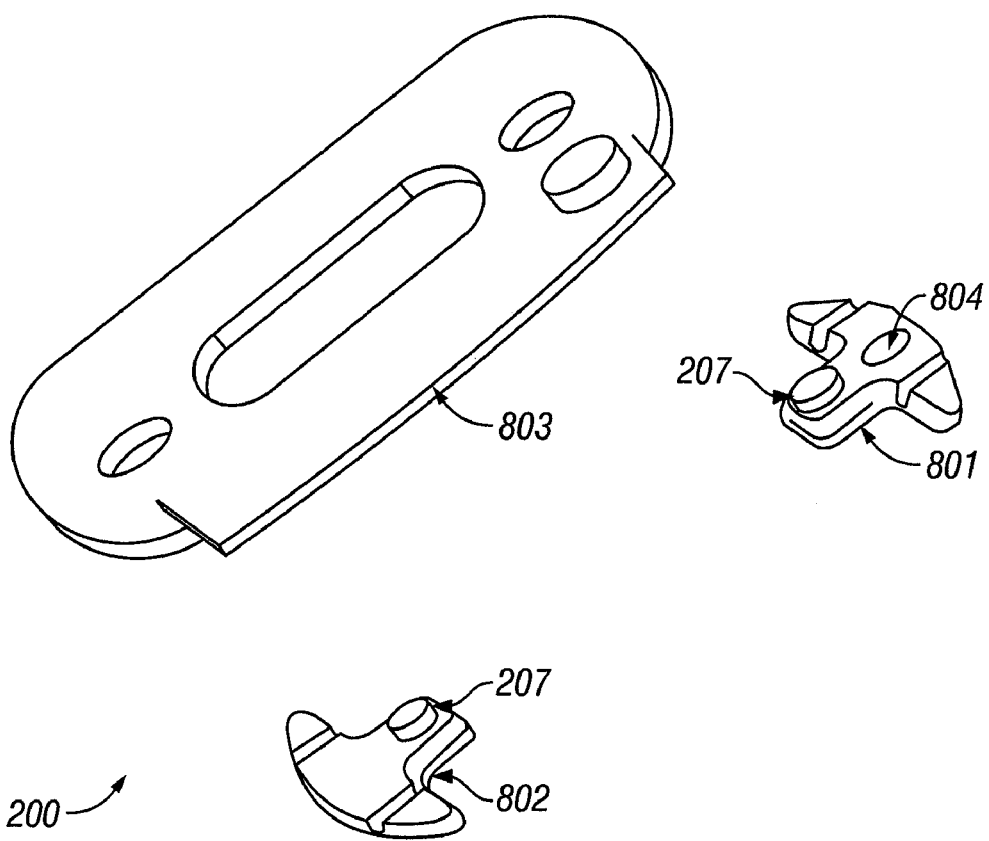
FIG. 8 illustrates a guide for alignment of a sample probe to a tissue site with two separate alignment pieces according to the invention.

A sixth embodiment of the invention uses a guide comprising two or more separate pieces, where each piece is semi-permanently and replaceably attached to a region about the sample site. Referring now to FIG. 8, a guide comprising a first alignment piece 801 and a second alignment piece 802 is presented. In this example, part of a housing of a sample probe 803 is presented. The sample probe is of any design. In this case, the aperture of the housing contains interfacing optics, such as illumination and collection optics. Optional magnets 207 are provided. In addition, an example of an optional registration indentation 804 is presented.

The first alignment piece 801 has registration points that control at least two of the x-, y-, and z-positions of the coupled sample probe. In a first example, the first alignment piece has a mechanical stop, such as a post. The sample probe has a corresponding mechanical stop, such as a post hole. When the sample probe is brought into contact with the first alignment piece, the post sets into the post hole in a lock and key fashion. The x-, y-, and z-positions of the sample probe are hence registered to a fixed position relative to the first alignment piece.

In a second example, the first alignment piece is one half of a lock and key mechanism, such as a ridge, that controls the x-, and z-position of the sample probe, which has the second half of a lock and key mechanism. In this instance, the z-position of the sample probe is not controlled because the trough on the sample probe that corresponds to the ridge on the alignment piece has freedom of movement along the y-axis.

A third example addresses the instance where a single alignment lock mechanism with rotational symmetry, such as a post, still allows rotational freedom. In the third example, the first alignment piece has one-half of a lock and key mechanism that does not have rotational symmetry, such as an isosceles triangle indentation. The sample probe has a second half of the lock and key mechanism corresponding to that of the first alignment piece, such as an isosceles triangle extrusion that fits into the oval indentation. In this third example, the x-, y-, and z-position and the rotational orientation of the sample probe are fixed relative to the sample site when aligned versus the first alignment piece. Additional registration means include ball bearings, kinematic mounts, hinges, slides, extrusions, indentations, and mechanical stops.

The second alignment piece 802 has means for registering the sample probe in any of the ways described, supra, for the first alignment piece. In particular, the second alignment piece controls at least one of the x-position, y-position, z-position, and rotational alignment of the corresponding sample probe.

A benefit of using two alignment pieces for a guide is that the sample is not fixed in size and/or orientation with time. For example, skin expands and contracts due to physical responses to outside parameters, such as fluid intake, hydration, body temperature, and environmental temperature. In the case of skin contract, a one piece guide causes the skin to stretch, which results in a changed optical pathlength and sampled volume by probing photons. For example, as skin stretches the skin layers, such as the epidermal and dermal layers, get thinner. This results in more photons penetrating through to the fat layer. Hence, the spectral features observed change, often with a loss of precision and/or accuracy of the corresponding glucose concentration estimations. In addition, changes in pathlength are often detrimental to precision and accuracy of resulting analyte concentration estimations. Use of two alignment pieces to register the position of an outside probe allows the skin to expand and contract without the limitation of a one piece guide holding two areas of skin a fixed distance apart.

In an example of a two part guide, the first alignment piece has a post 804 that controls the x-, y-, and z-position of the corresponding sample probe. The second alignment piece is a slide that controls the y-position and z-position of the corresponding sample probe. The sample probe aligns to the post of the first alignment piece. The sample probe also aligns to the y-position and z-position of the second alignment piece. As the sample site expands or contracts, the x-position of the probe on the second alignment piece is free to move. In a second example, the second alignment piece allows freedom of motion in the y-position. In a third example, the first alignment piece also controls the rotational freedom of the sample probe as described, supra. In a fourth example, an aperture of the sample probe creates a meniscus about the sample site at time of sampling.

Additional permutations and combination means for registering the sample probe relative to the first alignment piece are possible.

EXAMPLE I

Figure 9:
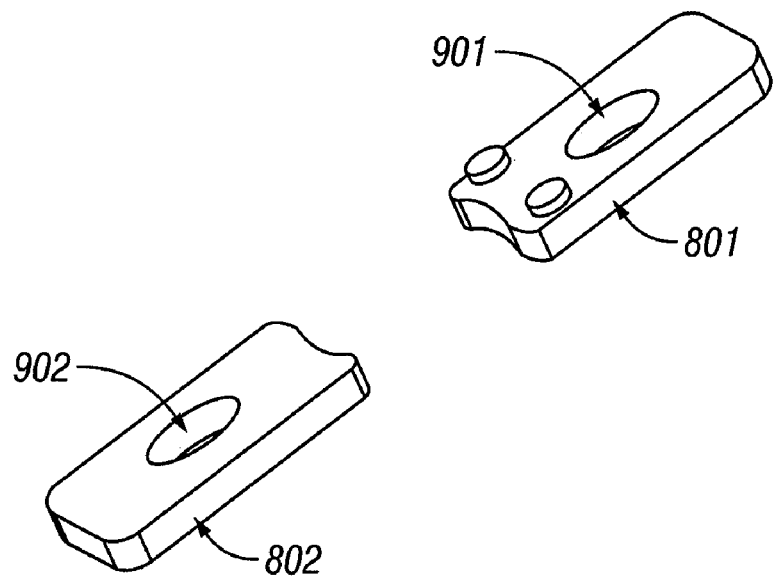
FIG. 9 illustrates a guide using magnets for alignment of a sample probe to a tissue site with two separate alignment pieces according to the invention.

Referring now to FIG. 9, a guide 200 with a first alignment piece 801 and a separate second alignment piece 802 is presented. In this example, the first alignment piece contains an optional magnet 901 that registers at least the x-, y-, and z-position of the sample probe. The second alignment piece also contains an optional magnet 902 and is used to register at least the y- and z-position of the sample probe. Together the first and second alignment pieces 801, 802 control the rotation of the corresponding sample probe relative to the guide and hence control the position of the sample probe relative to the sample tissue.

The first and second alignment pieces 801, 802 are optionally attached directly to a tissue sample site or a region about the sample site, as described supra. In another instance, one or more intermediate layers are placed between the first and second alignment pieces 801, 802 and the tissue sample.

Figure 10:
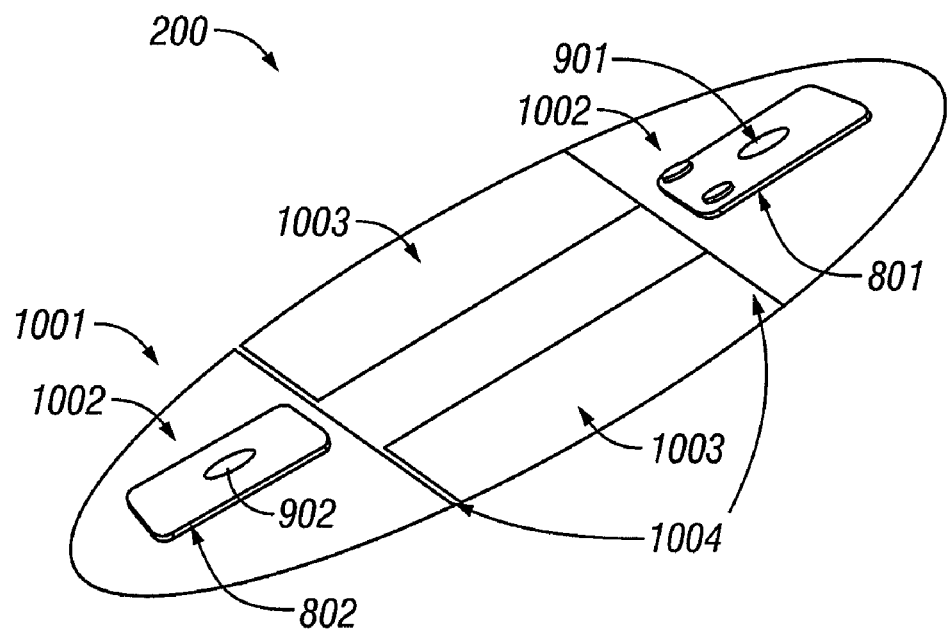
FIG. 10 illustrates a guide with a layer between an alignment piece and a sample site according to the invention.

Referring now to FIG. 10, a first layer 1001 is places on the sample side of the first and second alignment pieces 801, 802. In its broadest sense, the first layer is a material that covers at least part of the space between the alignment pieces and the tissue sample.

Several examples of first layers configurations are provided. In one case, the first layer 1001 is an adhesive, as described heretofore. In a second case, part of the first layer 1001 is composed of a flexible material 1002, such as acetate. In the embodiment pictured in FIG. 10, the flexible layer forms a living hinge, which helps to adapt the guide 200 to the changing shape of skin tissue and helps the guide 200 fit a curved surface. The living hinge also serves to distribute the weight of the guide and/or sample probe across a greater region of the skin tissue, especially as the sample probe is removed and replaced resulting in weight changes on or about the sample site. Preferably, the weight of the sample probe is distributed by the guide off of the sample site that is optically probed. In a third case, a separation section 1003 of the first layer is used to separate an adhesive layer from the sample probe, such as polytetrafluoroethylene. In a fourth case, a first section 1002, such as a flexible material section, and a second section 1003, such as a separation section are both used in the first layer 1001. In the pictured embodiment of FIG. 1—, the first and second sections 1002, 1003 are separated by a gap 1004. The gap allows the first layer to expand, contract, twist, and/or deform as the skin tissue shape changes.

The first layer serves at least one of several purposes. First, the first layer 1001 covers at least a portion of the second layer 1101, described infra, and protects the surface of the sample probe from the first layer. Second, the first layer 1001 is optionally separated into regions that are not attached by one or more small gaps 1004 allowing for fewer restraints on the skin tissue and hence fewer changes in the optical properties of the skin that affect optical based analyte concentration estimations.

Figure 11:
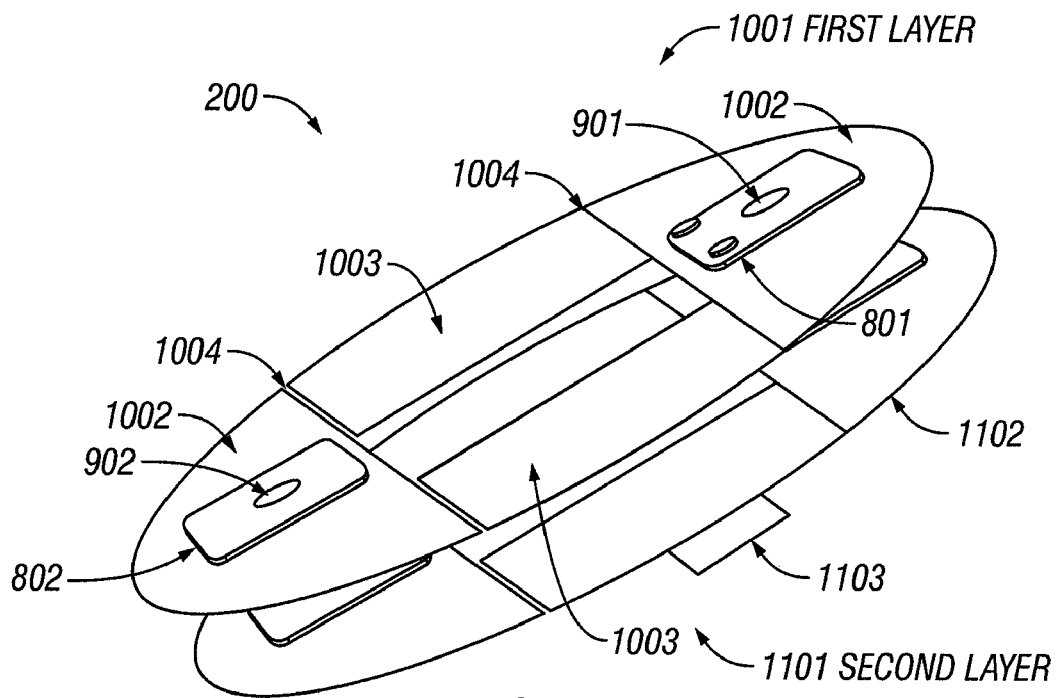
FIG. 11 illustrates a guide with two layers between an alignment piece and a sample site according to the invention.
Figure 12:
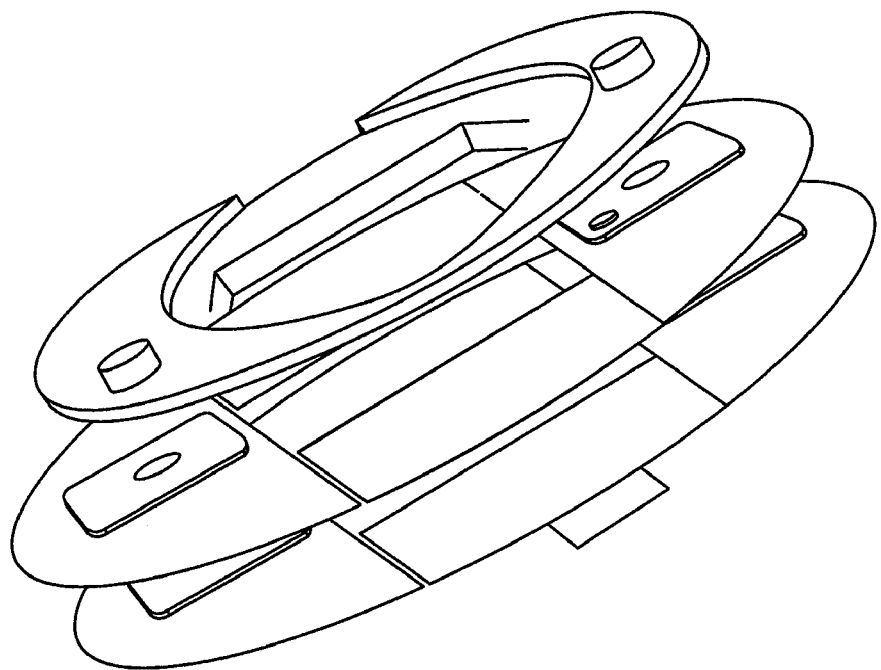
FIG. 12 presents a guide with two layers between an alignment piece and a sample site interacting with a sample probe according to the invention.

Referring now to FIG. 11, a second layer 1101 is placed on the sample side of the first layer. The second layer is either replaceably attached or permanently attached to the first layer. The second layer contains one or more sublayers. In a first case, a single sub-layer is used, such as an adhesive layer used to attach either the attachment pieces 801, 802 or the first layer 1001 to the tissue sample. In a second case, three sublayers are used, such as a substrate layer sandwiched by an adhesive layer on either side. A third case uses a peel-off layer on one or both sides of additional sub-layers for ease of attachment to any of the skin tissue, attachment pieces 801, 802, or first layer. In the embodiment of FIG. 11, a peel-off layer 1103 is on the sample side of the second layer 1101 and the second layer contains at least an adhesive layer 1102. An example of the guide presented in FIG. 11 interacting with a tip of a sample probe is illustrated in FIG. 12.

A particular embodiment uses a guide 200 that comprises at least a first and a second alignment piece 801, 802. A preferable embodiment also includes a first layer 1001 and a second layer 1101.

A guide 200 that includes at least a first and a second alignment piece 801, 802 is available as a disposable item in a kit. Preferably, the kit includes one or both of a first layer 1001 and an adhesive layer 1101.

EXAMPLE II

Figure 13:
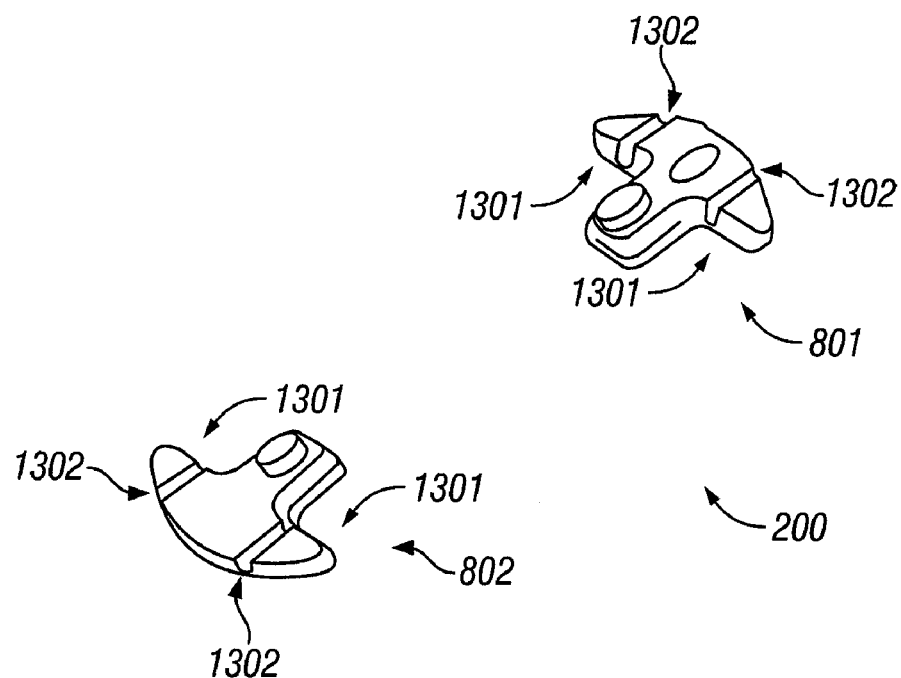
FIG. 13 illustrates a guide with at least one flexible part according to the invention.

Referring now to FIG. 13, a guide 200 comprised of two separate alignment pieces 801, 802 is presented. In this example, each of the two alignment pieces contains wings 1301. The wings are attached to the alignment pieces with a flexible material 1302, such as a living hinge. The living hinge compensates for changes in at least one of shape, weight, and applied pressure. In this example, means for alignment of at least one of an x-position, y-position, z-position, and rotational position are provided jointly by the two alignment pieces and/or separately be each of the alignment pieces.

Z-Axis Movable Guide

In an additional embodiment, rotation of the sample probe is controlled by the guide while allowing z-axis movement of the guide.

Figure 14A:
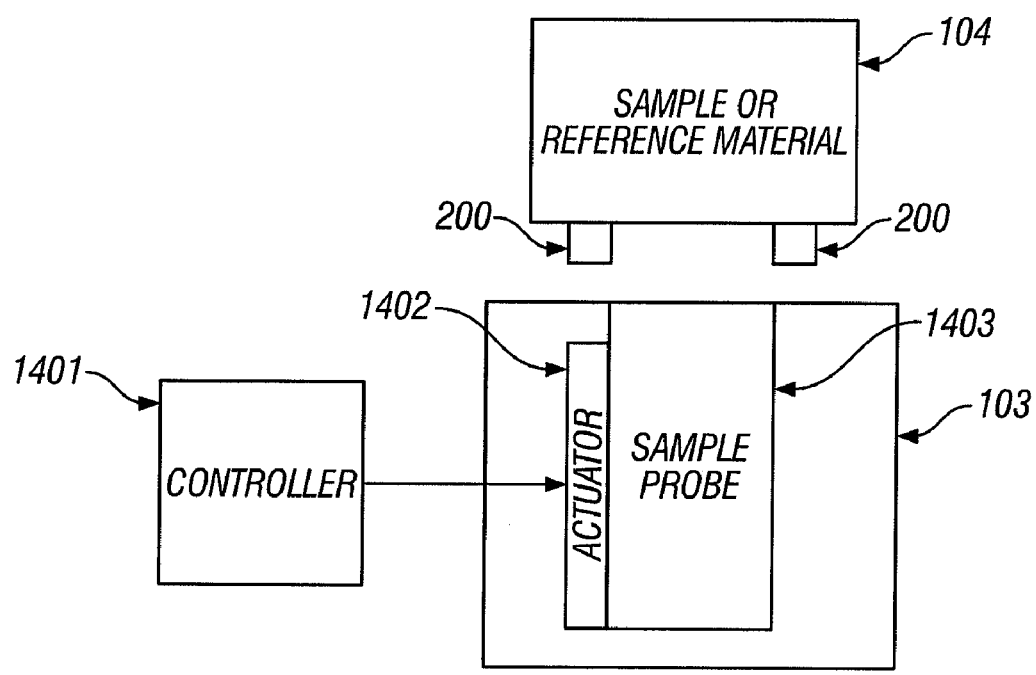
FIGS. 14 and 14b present a guide allowing a z-axis movable sample probe according to the invention.
Figure 14B:
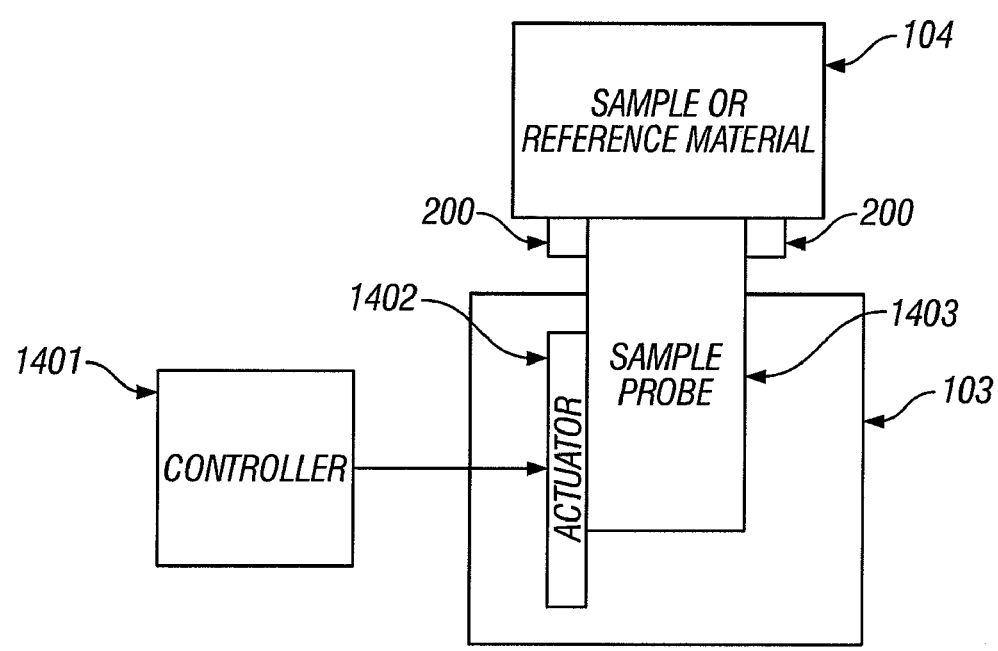

Referring now to FIGS. 14*a* and 14*b*, a schematic presentation of sample probe control and sample probe movement relative to a sample is presented. The sample module 103 includes a sample probe 1403. A controller 1401 controls an actuator 1402 that moves the sample probe 1403. Signal processing means result in a control signal that is transferred from the controller 1401 to the sample probe 1403 typically through an actuator 1402. The communicated control signal is used to control the z-axis movement of at least part of the sample module 103 relative to the tissue sample 104 or reference material. The part of the sample module movable along the z-axis is referred to as the sample probe or sampling probe 1403. In one case, the controller sends the control signal from the algorithm to the sample module actuator, preferably via a communication bundle. In a second case, the controller 1401 receives input from the sample probe or other sensor and uses the input to move the actuator 1402. Thus, in various embodiments, the controller is in different locations within the analyzer, such as in the sample module 103 or in the base module 101. In these cases, the actuator 1402 subsequently moves the sample probe 1403 relative to the tissue sample site 104. In a third case, no controller or actuator is used and the sample probe moves in response to gravity. The sample probe 1403 is typically controlled along the z-axis from a position of no contact, to a position of tissue sample contact, and optionally to a position of tissue sample displacement.

The sample probe 1403 is presented in FIG. 14 at a first (FIG. 14*a*) and second (FIG. 14*b*) instant of time with the first time presenting the sample probe when it is not in contact with the sample site. The second time presents the sample probe with minimal displacement of the sample tissue. The sample probe is, optionally, moved toward the sample, away from the sample, or remains static as a function of time as discussed, infra. An optional guide is attached to the sample and/or reference. Input to the controller includes a predetermined profile, an interpretation of spectral data collected from the sample probe, or input from a sensor, such as a pressure sensor, an optical sensor, or a thermal sensor.

Optical Registration

In an alternate embodiment, the guide provides a means for optical registration. In this embodiment, reflectors or light sensitive elements are placed onto the guide. The optical probe assembly is equipped with light sources and several detectors that allow the position of the guide to be accurately assessed, in either two or three dimensions. In a first configuration, two dimensions (x, y) are assessed and a mechanical stop is used to control the third dimension. In a second configuration, the location of the guide is optically assessed in all three dimensions (x, y, z). Because the position of the guide is constant with respect to the targeted tissue volume, the positional assessment provides accurate information regarding the location of the targeted tissue volume with respect to the optical probe. The registration information provided by such assessment is used to place the tissue site onto the optical probe, or vice versa, through any of the following means:

- An operator or user is given a visual or audible signal indicating how to move the tissue site with respect to the optical probe;
- A mechanical positioning system is used to position the tissue measurement site with respect to the optical probe; or
- A mechanical positioning system is used to position the optical probe onto the tissue measurement site.

Equilibration

In a further example, the guide contains any of a number of elements designed to enhance equilibration between the glucose concentration at the tissue sample site and a capillary site, such as the fingertip. Rapidly changing glucose concentrations as a function of time can lead to significant discrepancies between alternate site blood glucose concentration and traditional blood glucose concentrations, such as from a well perfused region such as finger. The concentration differences are directly related to diffusion and perfusion that combine to limit the rate of the equilibrium process. Equilibrium between the two sites allows for the use of glucose-related signal measured at an alternate site to be more accurate in estimation of finger blood glucose concentration.

A number of elements are, optionally, incorporated into the sample module and/or guide to increase sampling precision and to increase the net analyte signal for a glucose concentration estimation. These optional elements are preferably powered through the base module and communication bundle, but are alternatively battery operated. Equalization approaches include photonic stimulation, ultrasound pretreatment, mechanical stimulation, and heating and are described, infra. Notably, equilibration of the glucose concentration between the sampled site and a well-perfused region such as an artery or the capillary bed of the fingertip is not required. A minimization of the difference in glucose concentration between the two regions aids in subsequent glucose concentration determination.

Photonic Stimulation

The guide optionally contains one or more light emitting diodes (LEDs) that provide photonic stimulation at wavelengths that induce capillary blood vessel dilation. Photostimulation is used to aid in equilibration of alternative site glucose concentrations with those of capillary blood. By increasing the vessel dilation, and thereby the blood flow rate to the alternate site, the limiting nature of mass transfer rates and their effect on blood glucose differences in tissue is minimized. The resulting effect is to reduce the differences between the finger and the alternate site blood glucose concentrations. The preferred embodiment uses LEDs at about 890 nm in an array with control electronics set into the arm guide. Other example wavelengths include about 910 nm, or at regions where water or another sample constituent strongly absorb. The LED's are alternatively used in a continuous monitoring application where they are located in the probe sensing tip at the tissue interface. Due to the periods of excitation required for stimulation, the 890 nm LED is preferably powered by a rechargeable battery in the guide so that the LED may be powered when the communication bundle is not used.

Ultrasound

The guide optionally contains an apparatus capable of delivering ultrasound energy into the sample site. Again, this technique is used to aid in equilibration of alternative site glucose concentrations with those of capillary blood by stimulating perfusion and/or blood flow.

Mechanical Stimulation

The guide optionally contains an apparatus that provides mechanical stimulation of the sampled site prior to spectral data acquisition. One example is a piezoelectric modulator than pulses in an out relative to the skin surface a distance of about 5 to 60 μm and preferably 20 to 50 μm in a continuous or duty cycle fashion.

Thermal

The guide optionally contains a heating and/or cooling element, such as a strip heater or an energy transfer pad. Heating is one mechanism of glucose compartment equilibration. These elements are used to match the core body temperature, to manipulate the local perfusion of blood, to avoid sweating and/or to modify the distribution of fluids among the various tissue compartments. As an example, the guide and/or plug contains a heating element that warms the nominally cooler skin surface to approximately body temperature. Example temperatures are about 88, 90, 92, 94, 96, and 98 degrees Fahrenheit. By continually warming the sample site or region about the sample site, the capillaries are dilated and glucose concentrations at the sample site to correlate with glucose concentrations in venous or well perfused capillary regions.

It is recognized that the sampling module is optionally brought into contact with the sample site without the use of a guide.

Measurement Site Occlusion

In still yet another embodiment, a guide aperture is filled with a removable plug. The contact of a window or plug with the skin stabilizes the tissue by providing the same tissue displacement as the probe and increases the localized skin surface and shallow depth hydration. As opposed to the use of a removable plug, use of a contact window allows a continuous barrier for proper hydration of the sampling site and a constant pressure interface. The use of a plug or contact window leads to increased precision and accuracy in glucose determination by the removal of issues associated with dry or pocketed skin at the sampling site.

When the tissue site is not being interfaced to the optical probe an occlusion plug 204 is normally inserted into the aperture 202. The occlusion plug penetrates into the aperture to the same extent as the optical probe and thereby creates a stable tissue state by simulating the contact energy of the optical probe. As discussed previously, the occlusion plug is composed of a material that provides a hydration barrier, thus promoting the full and stable hydration of the stratum corneum. In the preferred embodiment, the plug is composed of the same material as the guide and possess a mechanical stop 205 to control the penetration into the tissue site. The size of the portion of the plug that is inserted into the aperture 206 is matched to the portion of the optical probe that is received by the guide aperture 202. Attachment of the plug to the guide may be through the use of one or more magnets located in both the guide and plug assemblies 207. However, other methods of attachment may be used, such as hook and loop, adhesives, and snaps. Alternately, the plug can be composed of a material that is elastic in nature and is kept in place by virtue of its tight fit into the guide aperture. Also, the plug can be a hydrophobic material, such as cellophane.

From the foregoing, one of ordinary skill in the art will recognize that an important aspect of the optical sampling system is the maintenance of an optimal level of hydration of the surface tissue at the measurement site for enhancement of the optical signal, sample reproducibility, and suppression of surface reflectance. The preferred embodiment of the hydration mechanism is by occlusive blockage of trans-epidermal water loss. This blockage ensures a steady state hydration as water diffusing from interior tissue is trapped in the stratum corneum. Attainment of high hydration levels reduces the water concentration gradient that provides the driving force for this trans-epidermal water movement. Thus, the above described occlusive plug fits snugly into the guide aperture during periods between measurements, acting to insulate the tissue in the guide aperture from trans-epidermal water loss and the environmental effects of temperature and humidity that are known to influence the stratum corneum hydration state. In addition to the preferred embodiment just described, an in alternate embodiment, wrapping a flexible polymer sheet (an occlusion patch) around the measurement site may also be used to attain a highly hydrated state via occlusion.

Other solutions to the problem of maintaining hydration of the stratum corneum, consistent with the spirit and scope of the invention are possible, including, but no limited to:

A vapor barrier or semi-permeable membrane (for example, GORE-TEX, manufactured by W. L. Gore and Associates of Newark, Del. as the mount) in the form of a wrap or a patch configured to cover the site target for measurement. In this latter embodiment, the patch is affixed to the tissue site through an adhesive or other attachment mechanism such as a strap or a wrap;

Non-occlusive mechanisms for hydration of the stratum corneum may also be used, including:

An application of water that is pneumatically driven into the skin;

Ultrasound energy applications to accelerate passive occlusion;

Topical application of skin toners and other water/solute mixtures such as alpha hydroxy acid solutions that serve to drive water and solute into the dry outer skin layer; and Topical analgesic formulations that enhance and/or stimulate local circulation at the measurement site leading to an improvement in surface hydration.

The mechanisms for achieving stratum corneum hydration may also be used in coupled treatments. For example, skin toner solution or an ultrasound energy application may be used in conjunction with an occlusive plug.

After an initial measurement is made, as described above, subsequent measurements are made by placing the tissue site onto the noninvasive measurement device, after removing the occlusion plug and allowing the guide to provide mechanical registration. After the optical tissue measurement is performed, the tissue is taken away from the device and the occlusion plug is re-inserted.

Meniscus

In addition to improving the precision of the probe placement event during the course of multiple measurements, the guide aperture induces the formation of a tissue meniscus, an upward bulge of tissue into the optical probe aperture. The tissue meniscus, a bulge of subsurface water forced into the aperture by the guide aperture, resulting from a relative difference in the contact pressure at the guide adhesion surface and the guide aperture, both provides for limitation of the penetration of the probe into the tissue and guarantees a highly compliant and energy absorbing contact event.

The hydrostatic pressure within the tissue in the aperture is greater than that on the nude (guideless) tissue sample. This increased hydrostatic pressure absorbs energy translated to the tissue when the probe contacts the tissue, thus limiting the resulting distortion of dermal collagen tissue. Distortion of dermal collagen has a strong effect on the tissue optical properties and thus the sampled tissue volume. To achieve this correction, the termination of the optical probe should be flush with the contact surface at the tissue measurement site when the optical probe is fully seated.

Coupling Medium

The interface between the optical probe and the skin surface at the tissue measurement site can also be a significant source of sampling error. Because the underlying tissue is not homogenous, the surface skin at the tissue measurement site may be uneven, with frequent irregularities. Coupling the relatively smooth surface of the optical probe with the irregular skin surface leads to air gaps between the two surfaces. The air gaps create an interface between the two surfaces that adversely affects the measurement during optical sampling of tissue. An amount of a coupling medium such as a coupling fluid between the optical probe and the skin of the tissue measurement site or sample site eliminates such gaps.

Preferably, the coupling fluid:
Is spectrally inactive;
Is non irritating and nontoxic;
Has low viscosity for good surface coverage properties; and
Has poor solvent properties with respect to leaching fatty acids and oils from the skin upon repeated application.

It is possible to achieve such characteristics by selecting the active components of the coupling fluid from the class of compounds called perfluorocarbons, i.e. those containing only carbon and fluorine atoms. Nominally limiting chain length to less than twenty carbons provides for a molecule having the requisite viscosity characteristics. The molecular species contained in the perfluorocarbon coupling fluid may contain branched or straight chain structures. A mixture of small perfluorocarbon molecules contained in the coupling fluid as polydisperse perfluorocarbons provides the required characteristics while keeping manufacturing costs low.

In a preferred embodiment, the coupling fluid is a perfluoro compound, a fluorocarbon, a perfluorocarbon, or a narrowly defined group of fluorocarbons in terms of viscosity, such as those known as FC-40 and FC-70, manufactured by 3M Corporation (St. Paul, Minn.). Such compounds are inactive in the near-infrared region, rendering them particularly well suited for optical sampling procedures employing near-infrared spectra. Additionally, they have the advantage of being non-toxic and non-irritating. Thus, they can come into direct contact with living tissue, even for extended periods of time, without posing a significant health risk to living subjects. Furthermore, perfluoro compounds of this type are hydrophobic and are poor solvents. Therefore, they are unlikely to absorb water or other contaminants that adversely affect the result during optical sampling. It is preferable that the sampling fluid be formulated without the addition of other substances, such as alcohols or detergents, which may introduce artifacts into the optical sample. Finally, the exceptional stability of perfluoro compounds eliminates the environmental hazard commonly associated with chlorofluorocarbons.

Other fluid compositions containing perfluorocarbons and chlorofluorocarbons are also suitable as coupling fluids. For example, a blend of 90% polymeric chlorotrifluoroethylene and 10% other fluorocarbons has the desired optical characteristics. Chlorotrifluoroethylene could also be used. While these compositions have the desired optical characteristics, their toxicity profiles and their solvent characteristics render them less desirable than the previously described perfluoro compounds.

Additionally, other fluid media are suitable for coupling of an optical probe to a tissue measurement site, for example, skin toner solutions or alpha hydroxy-acid solutions.

During use, a quantity of sampling fluid is placed at the interface of the tissue measurement site and the fiber optic probe so that the tissue measurement site and the fiber optic probe may be tightly coupled without leaving any air spaces between the two surfaces. In practice, one convenient way of placing the quantity of the sampling fluid at the interface between the tissue measurement site and the probe is to place a small amount of the fluid on the skin surface prior to placing the fiber optic probe, although it is easier to place it on the fiber-optic probe.

Furthermore, certain non-fluid media having the requisite optical characteristic of being near-infrared neutral are also suitable as coupling media, for example, a GORE-TEX membrane interposed between the probe and the surface of the measurement site, particularly when used in conjunction with one of the fluid media previously described.

Bias Correction

Finally, a bias correction is preferably made to the measurement to account for variations in the size of the meniscus caused by the guide installation. These bias corrections are applied to the processed spectral measurement and to the predicted analyte value just prior to prediction.

A noninvasive measurement system provides a tissue measurement, $m \in \Re^{1 \times N}$ where N corresponds to the dimensionality of the measurement. In the preferred embodiment, m refers to the intensity spectrum of the tissue sample represented by the intensity at N wavelengths, or wavelength ranges or selected wavelengths selected from a wavelength range, for example 700-2500 nm. In the preferred embodiment, a background or reference, $m_o$, is used to standardize or normalize the tissue measurement according to the calculation $$a = \log_{10} \frac{m}{m_o} \quad (2)$$

where $m_o$ is an estimate of light incident on the sample, m is an intensity spectrum of light detected and a is analogous to an absorbance spectrum containing quantitative information that is based on the known interaction of the incident light with components of the body tissue. Alternately, the tissue measurement, m, can be used directly instead of a.

The standardized tissue measurement, a, is preferably preprocessed to attenuate noise and to reduce the interference related to surface reflectance, tissue volume distortion, and instrumental effects to produce the processed tissue measurement, x. In the preferred embodiment, the preprocessing steps include calculating the first derivative, selecting specific wavelengths and wavelength regions specific to the analyte of interest, and performing scatter correction or multiplicative scatter correction.

A bias correction step follows the preprocessing steps defined above through the determination of the difference between the preprocessed estimated tissue background—the tissue template, and x through $$z = x - (cx_1 + d) \quad (3)$$

where x is the preprocessed tissue measurement or the selected set of features, $x_1$ is the estimated background or tissue template associated with the current guide placement, and c and d are slope and intercept adjustments to the tissue template. After each guide placement, the tissue template is determined through one or more tissue measurements (after preprocessing) and a data selection criterion for example by selecting only tissue measurements that resemble each other closely and averaging them. In the preferred embodiment, $x_t$ is calculated from a single tissue measurement that is collected after an equalization period following the placement of the guide and c=1 and d=0. This process is referred to as bias correction and involves both:

The collection of one or more tissue measurements that are processed to form a tissue template; as well as An associated set of reference analyte values determined from a primary analyte measurement source.

For example, in the case of near-infrared measurement of glucose, the reference analyte values are determined from an electrochemical analysis of blood draws. The analyte values are combined, according to the same strategy as that used to create the tissue template to form an analyte measurement bias adjustment, b, through the equation $$\hat{y} = g(z) + b \quad (4)$$

where g: $\Re^M \to \Re^1$ is a calibration model used to map z to an estimate of the target analyte. The model is determined from a calibration set of exemplary paired data points, each consisting of a pre-processed and bias corrected tissue measurement (z) and an associated reference analyte value (y) determined from an analysis of a blood or interstitial fluid sample. According to this process, blood, serum, plasma, or interstitial draws are taken from a tissue site that is either near the sensor sample site or has been designed/determined to reflect the sample site. For example, when non-invasive near-infrared measurements for the purpose of glucose measurement are taken for calibration on the forearm, it is possible in some individuals to collect a capillary blood draw from the same forearm or an alternate site such as opposite forearm. Alternately, rather than using blood draws, it is beneficial in some instances to use interstitial glucose values rather than capillary glucose values. The method for designing the structure of g is through the process of system identification [L. Ljung, *Systems Identification: Theory for the User*, 2d.ed., Prentice Hall (1999)]. The model parameters are calculated using known methods including multivariate regression or weighted multivariate regression [N. Draper, H. Smith, *Applied Regression Analysis*, 2d. ed., John Wiley and Sons, New York (1981)], principal component regression [H. Martens, T. Naes, *Multivariate Calibration*, John Wiley and Sons, New York (1989)], partial least squares regression [P. Geladi, B. Kowalski, *Partial least-squares regression: a tutorial*, Analytica Chimica Acta, 185, pp. 1-17, (1986)], or artificial neural networks [S. Haykin, *Neural Networks: A Comprehensive Foundation*, Prentice Hall, Upper Saddle River N.J. (1994)]. Calibration data must also be bias corrected if data contains subsets associated with different guide placement events.

Optionally, the bias corrected tissue measurements undergo an outlier detection step. The necessity for outlier detection and the form of an outlier detection procedure are dependent on the sampling technology employed. Outlier detection provides a method of detecting invalid measurements through spectral variations that result from problems in the instrument, poor sampling of the subject or a subject outside the calibration set. One method of detecting outliers is through a principal component analysis and an analysis of the residuals.

Exemplary Applications

EXAMPLE 1

A study was performed to examine the difference in spectral variation between several different near-infrared sampling treatments on a single subject. Near-infrared spectra were collected using a custom built scanning near-infrared spectrometer that collected intensity spectra in diffuse reflectance over the wavelength range 1100-1950 nm. The spectral sampling interval was one nanometer and the signal-to-noise ratio at the peak intensity was approximately 90 dB. The detector used in the study was Indium-Gallium-Arsenide (InGaAs) and the optical configuration consisted of a simple fiber optic interface to the skin with a small (<2 mm) distance between the illumination and detection fibers. Reference spectra were recorded before each sample measurement by scanning a 99% SPECTRALON reflectance material provided by LABSPHERE of North Sutton, N.H. The absorbance spectrum was calculated through Equation (2), supra.

Approximately twenty near-infrared absorbance spectra were collected on the subject's forearm using the following treatments:

1. Baseline measurements using only elbow and wrist supports to guide the patient's arm placement;
2. Measurements were taken using the preferred embodiment of the guide positioning system herein described, without occlusion of the measurement site; and
3. Both the guide positioning system and the disclosed method of occlusion, i.e. a plug in the aperture of the guide.

Before the collection of each spectrum, the subject's arm was replaced on the optical probe. Analysis of the data was performed on each of the three data subsets described above and consisted of calculating the root mean square variation at each motor position of the spectrometer. The root mean square variation without the guide positioning system shows relatively more sample variation. The relative variation related to replacement of the subjects arm on the optical probe is reduced by use of the guide (Control 1) and still further reduced through the addition of site occlusion (Control 2).

EXAMPLE 2

As a further illustration of the benefit of the guide placement system, sixty measurements were performed on a single subject with and without the guide positioning system. All spectra were collected using a custom built scanning near-infrared spectrometer. The instrument collected intensity spectra in diffuse reflectance from the forearm in the wavelength range 1050-2450 nm. The spectral sampling interval was 1 nm and the signal-to-noise ratio at the peak intensity was approximately 90 dB. The detectors used in the study were a combination of Indium-Gallium-Arsenide (InGaAs) and extended InGaAs detectors. The optical configuration consisted of a simple fiber-optic interface to the skin with a small (<2 mm) distance between the illumination and detection fibers. Reference spectra were recorded prior to each sample measurement by scanning a 99% SPECTRALON reflectance material and absorbance was calculated according to Equation (2). A cradle was developed to position the arm over the sample interface in a reproducible location with a reproducible degree of pressure, with the subject remaining seated during the experiment. In the first set of measurements, 60 samples were collected, each representing a different arm placement and absorbance was calculated. In the second set of measurements, 60 samples were collected with the use of the guide positioning system. The absorbance spectra illustrate the benefit of using the guide positioning system. The absorbance spectra over the 60 arm placements without the use of the guide positioning system. When the guide was used, the amount of spectral variation is significantly reduced.

EXAMPLE 3

As a test of the benefit of the method of occlusion, 60 measurements were performed on a single subject. In the first set of measurements, 60 samples were collected using the guide positioning system without occlusion and absorbance was calculated as previously described. In the second set of measurements, 60 samples were collected with the use of both the guide positioning system and the preferred method of occlusion, i.e. a plug in the guide aperture. The decrease in surface variation associated with the water bands demonstrated the improved optical sampling realized as a result of the method of occlusion.

While the invented optical probe placement guide allows highly repeatable probe placement at a targeted tissue measurement site, the invention may also be used to produce small sampling variations in a controlled manner by shifting the placement of the optical probe in known increments across successive optical samples.

The invention provides a means of limiting sampling errors during in-vivo spectroscopic examination of tissue samples by providing highly repeatable optical probe placement at a targeted tissue measurement site.

Embodiments of the invention use a guide that does at least one of:
  Inducing the formation of a tissue meniscus, created by the pooling of epidermal water in the guide aperture due to the relative difference in the contact pressure at the guide adhesion surface and the guide aperture, where no part of the guide contacts the tissue;
  Minimizing interference due to surface irregularities and controls variation in the volume of tissue sampled;
  Using a two-part guide system;
  Using a guide that controls rotation of a sample probe and allows z-axis movement of the probe;
  Using a separate base module and sample module in conjunction with a guide;
  Using a guide that controls rotation; and
  Using a guide with two or more layers.

Structural features of the invention minimize temperature fluctuations and variable stratum corneum hydration at the tissue measurement site. In addition, structural features of the invention minimize variations in optical probe placement and variations due to tissue distortion and displacement. These minimizations each reduce sampling error. An optional temperature probe in direct contact with the skin surface at the tissue measurement site allows the monitoring of skin temperature across successive measurements. An optical coupling fluid eliminates air spaces at the interface of the skin surface of the tissue measurement site and the optical probe. A fully hydrated stratum corneum is attained by the use of an occlusive plug or other mechanism. Finally, spectral measurements, and resulting analyte measurements are bias corrected to compensate error resulting from guide placement.

While the invented optical sampling interface system has been herein described in relation to optical sampling of tissue, one skilled in the art will appreciate that the invention may be applied in other settings requiring repeatable placement of an optical probe.

It is understood that each of the elements of the optical probe placement guide measurement system herein described are individually beneficial to the measurement and therefore can be used with or without the other elements. Specifically, the guide, the hydration control system, the coupling fluid, and the bias correction are uniquely beneficial. For example, in the event that an alternate mechanical positioning system is developed, the hydration control process, bias correction, and the coupling fluid are still beneficial.

Although the invention is described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A guide for positioning a sample probe at a targeted measurement site, wherein said sample probe comprises a single sample probe tip, said guide comprising:
  a first alignment piece having a contact surface, at least a portion of said contact surface being in contact with a surface proximate said measurement site during use; and
  a second alignment piece not directly attached to said first alignment piece, said second alignment piece being in contact with said surface proximate said measurement site during use;
  said first alignment piece and said second alignment piece comprising means for rotational alignment of said sample probe with respect to said alignment pieces;
  wherein rotational of said sample probe is not required to position said sample probe at said measurement site, and
  wherein said first alignment piece and said second alignment piece jointly control rotation alignment of said sample probe.

2. The guide of claim 1, wherein said sample probe tip comprises an optical probe tip.

3. The guide of claim 2, further comprising means for registering any of x-, y-, and z-location of said sample probe with respect to said alignment piece.

4. The guide of claim 1, wherein said guide comprises at least one flexible member.

5. The guide of claim 1, wherein said second alignment piece comprises:
  means for registering y-location and z-location of said sample probe with respect to said measurement site.

6. The guide of claim 1, wherein said means for rotational alignment comprises magnetic registration means along any of x-, y-, and z-axes.

7. The guide of claim 1, further comprising:
  means for stabilizing skin surface temperature.

* * * * *